United States Patent [19]

Roberts et al.

[11] 4,033,339
[45] July 5, 1977

[54] CERVICAL SIDE POSTURE TABLE HAVING EFFECTIVE HEAD RESTRAINT MEANS

[75] Inventors: William Powell Roberts, Tampa, Fla., Gratz Linwood Roberts, Jr., Adelphi, Md.

[73] Assignee: said William P. Roberts, by said Gratz L. Roberts

[22] Filed: Aug. 12, 1975

[21] Appl. No.: 604,030

[52] U.S. Cl. .................................. 128/68; 128/73; 269/328
[51] Int. Cl.² .......................................... A61F 5/00
[58] Field of Search .................. 128/68, 69, 70, 71, 128/72, 73, 74, 133, 134, 83; 269/323, 322, 324, 325, 328; 248/118

[56] References Cited

UNITED STATES PATENTS

| | | | |
|---|---|---|---|
| 1,735,703 | 11/1929 | Williams | 128/73 |
| 2,091,014 | 8/1937 | Saak | 128/73 |
| 2,172,941 | 9/1939 | Manning et al. | 128/73 X |
| 2,217,783 | 10/1940 | Bell | 128/73 |
| 2,715,557 | 8/1955 | Rock | 269/328 X |
| 3,004,812 | 10/1961 | Miller | 269/323 |
| 3,521,057 | 7/1970 | Morlan | 250/50 |
| 3,572,835 | 3/1971 | Kees, Jr. et al. | 269/328 |
| 3,822,875 | 7/1974 | Schmedemann | 269/323 |
| 3,845,946 | 11/1974 | Warden et al. | 269/323 |

*Primary Examiner*—John D. Yasko

[57] ABSTRACT

A novel side-posture table for use by chiropractors and other members of the healing arts in order to relieve the patient from the pain and suffering resulting from displaced portions of the upper-cervical section of his or her spine. A novel headrest portion is provided, with respect to which the head of the patient can be painlessly immobilized, thus enabling the chiropractor to apply adjustic thrusts as may be necessary in the proper treatment of a patient without the patient's head tending to move undesirably at such times, which motion would have the effect of greatly diminishing the value of the adjustment being made. Inasmuch as accurate and very precise movements of the atlas vertebra are to be brought about, the design of our machine is such as to enable the patient to lie on either side, facing the direction appropriate for his circumstances. Advantageously, our novel headrest arrangement can be selectively varied in a heightwise sense in order to dispose the patient's vertebral members between the upper-cervical and the mid-cervical spine in the most appropriate configuration from the standpoints of his conditions of vertebral displacement and the type of adjustic remedy to be applied. In addition, the headrest can be moved in tilt at the behest of the chiropractor until such time as the novel mastoid support portion of the headrest is in such position with respect to the mastoid bone of the patient as to minimize any tendency of the head to rock or tilt during the administration of the forthcoming treatment. Additionally, our novel machine utilizes an electrical push-button arrangement such that the chiropractor can make rapid yet precise movements of the headrest so as to best accommodate the patient, with an ancillary feature of our invention involving an automatic regime, in which the headrest can be caused to automatically return to the height and tilt positions previously found to be optimum for the patient about to undergo treatment.

30 Claims, 38 Drawing Figures

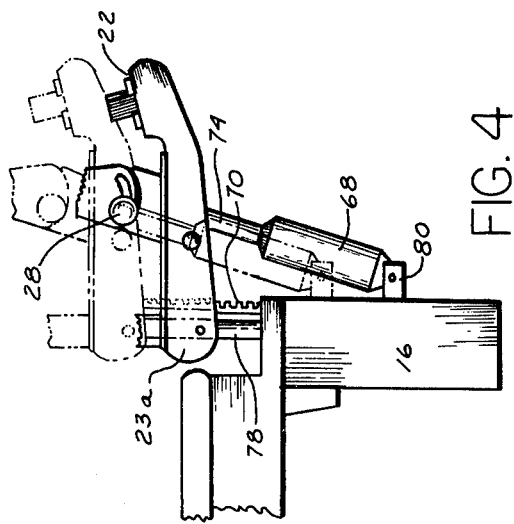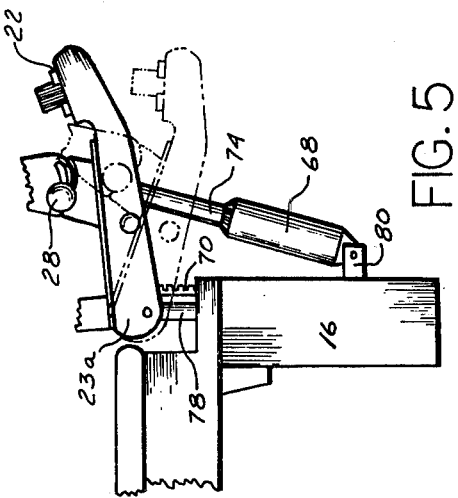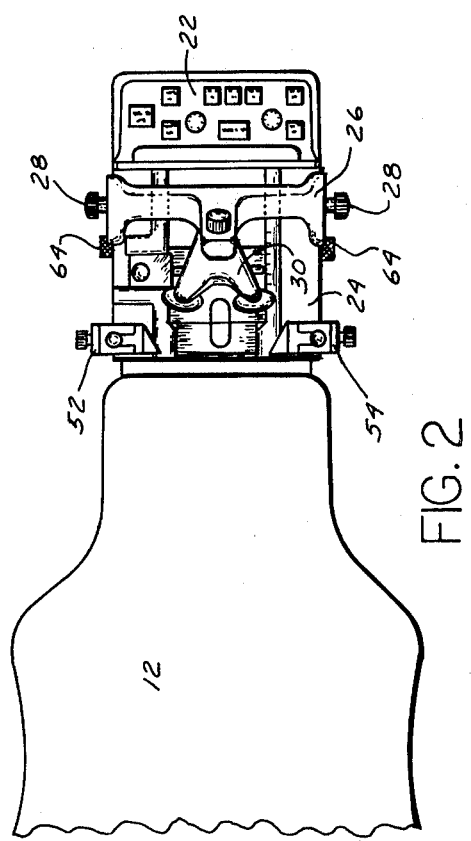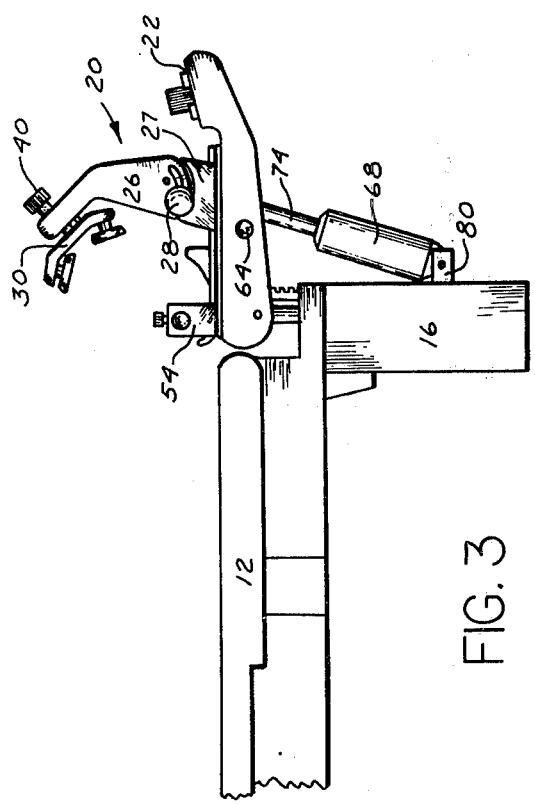

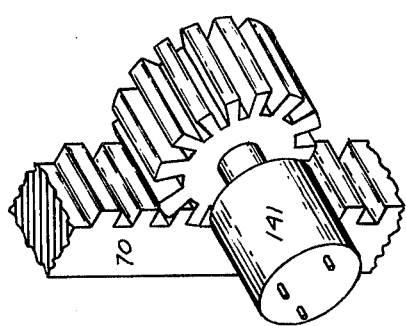
FIG. 7-A
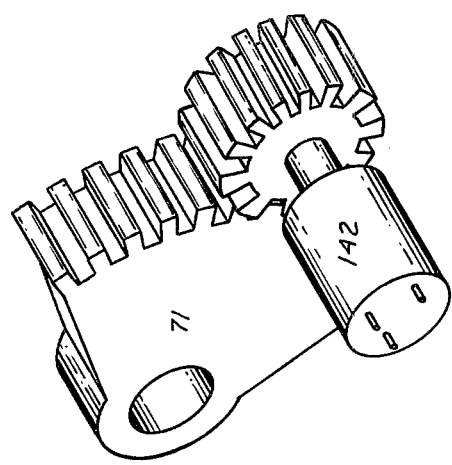
FIG. 7-B
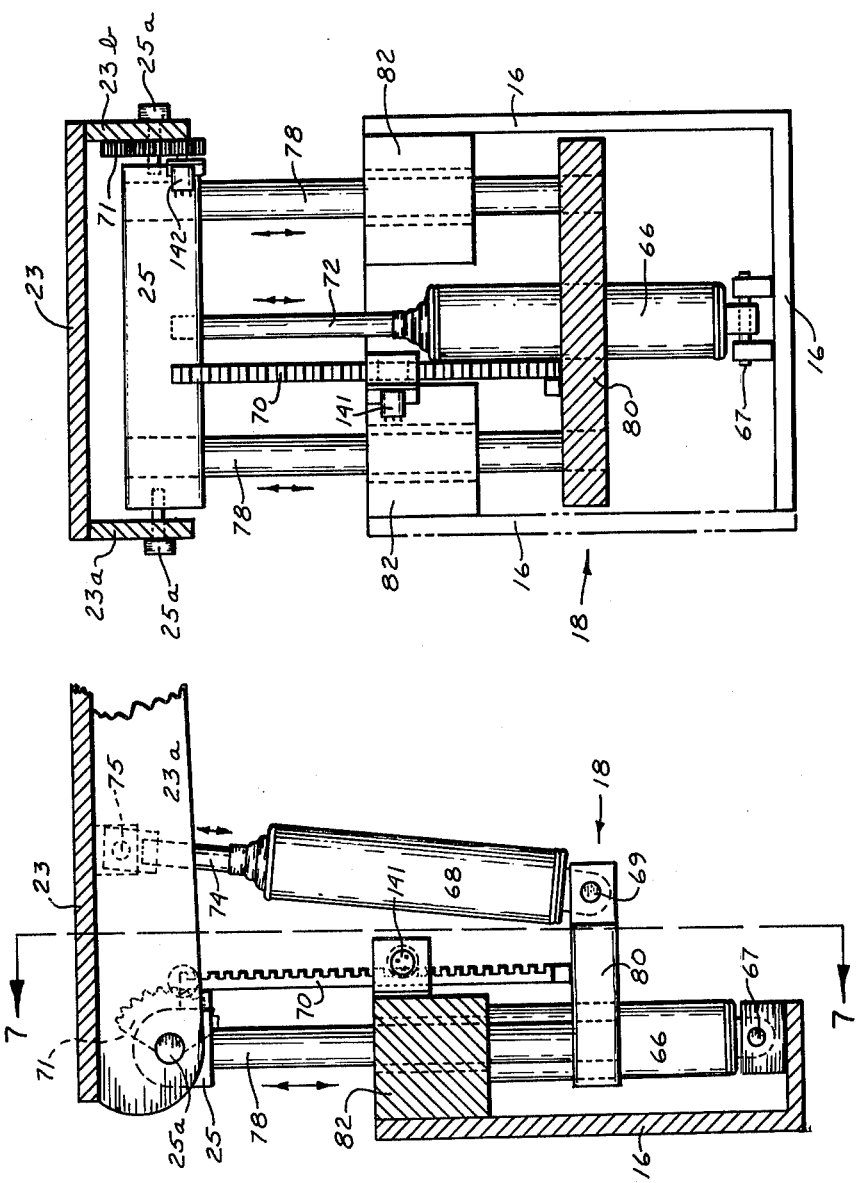
FIG. 7
FIG. 6

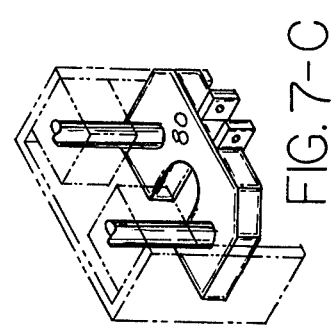
FIG. 7-C
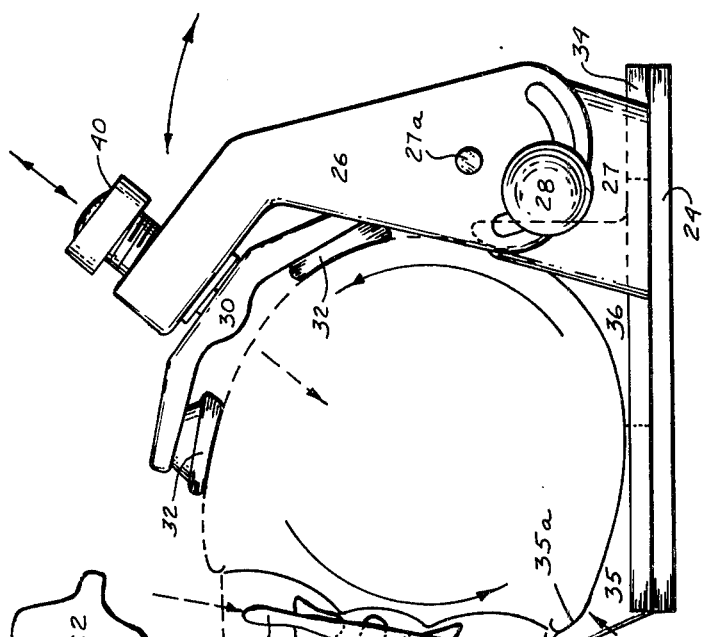
FIG. 9
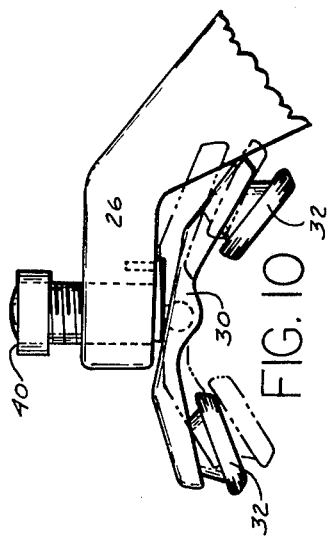
FIG. 10
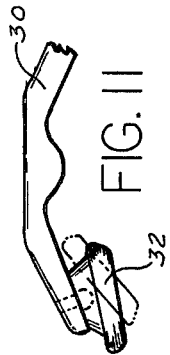
FIG. 11
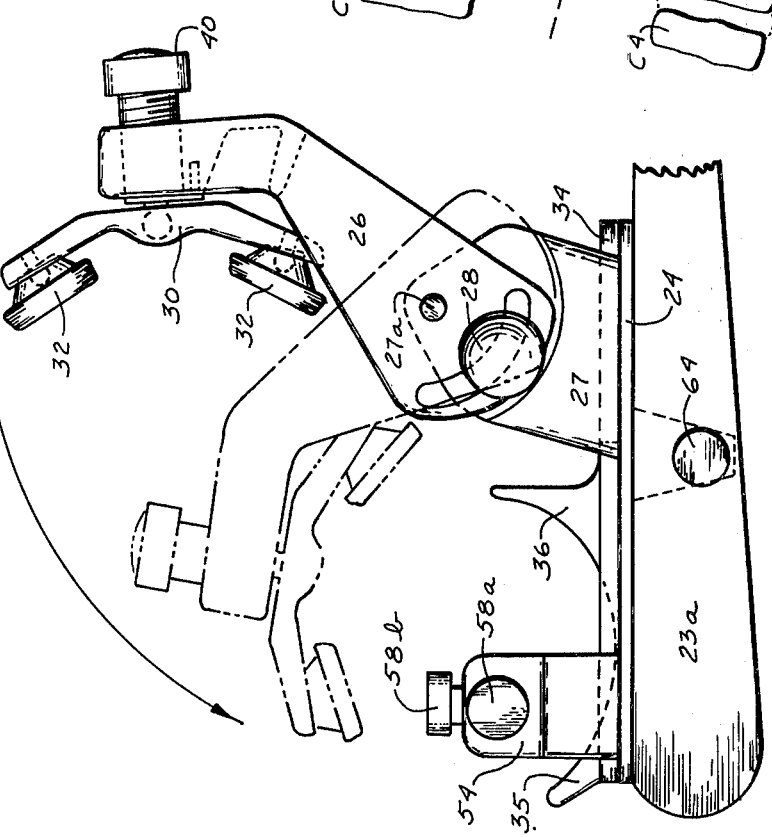
FIG. 8

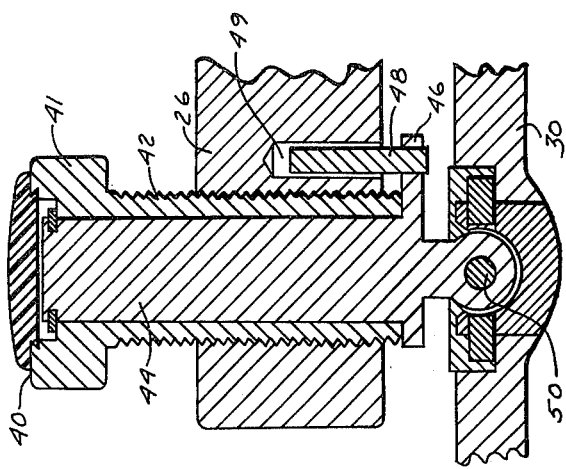
FIG. 14
FIG. 13-A
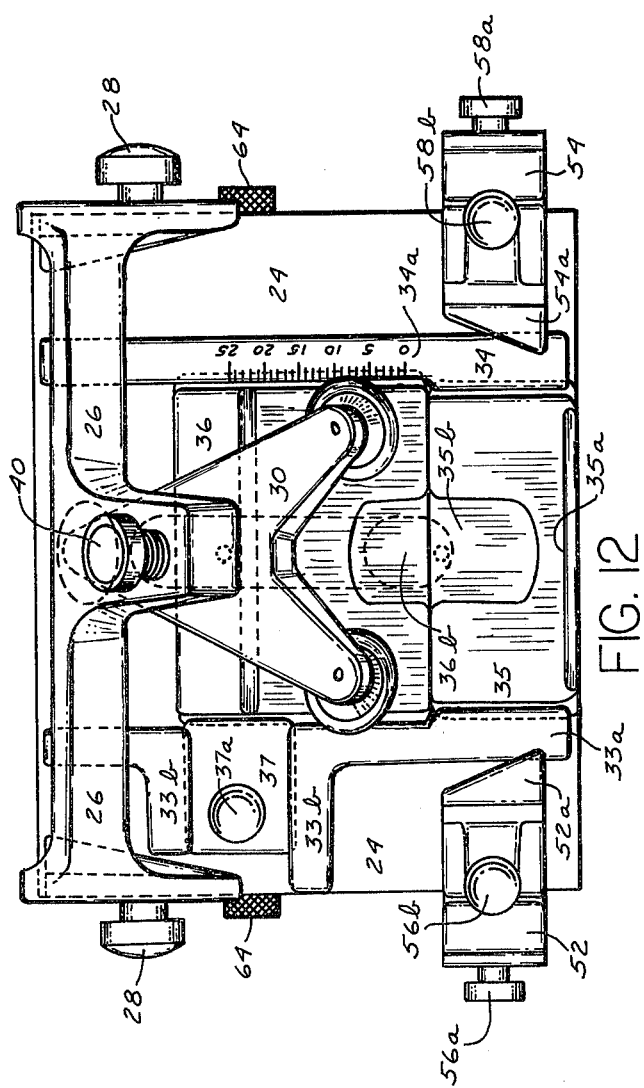
FIG. 12
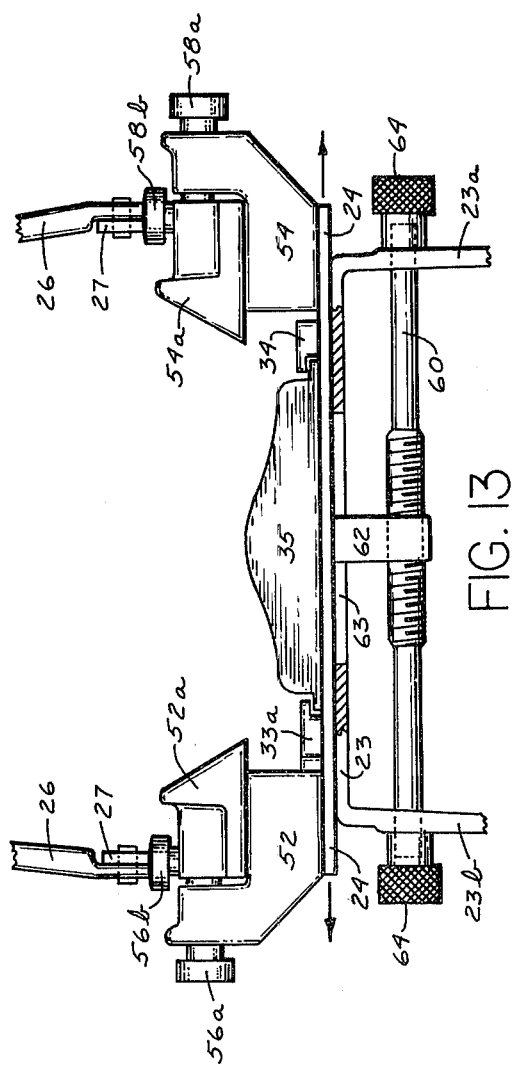
FIG. 13

| MODEL | A | B | C | D | E | F | G |
|---|---|---|---|---|---|---|---|
| BABY | 3.5 O.D. 15° | .500 | 1.25 O.D. 25° | 1.75 O.D. 20° | 4.5 O.D. 60° | .643 | 5° |
| ADOLESCENT | 3.75 O.D. 18° | .630 | 1.375 O.D. 30° | 1.875 O.D. 20° | 5.0 O.D. 60° | .715 | 7½° |
| ADULT | 3.75 O.D. 20° | .780 | 1.5 O.D. 35° | 2.0 O.D. 20° | 5.5 O.D. 60° | .786 | 10° |
| LARGE | 3.75 O.D. 22° | .880 | 1.75 O.D. 40° | 2.0 O.D. 20° | 6.0 O.D. 60° | .857 | 12½° |
| EXTRA LARGE | — | .880 | 1.75 O.D. 40° | — | 6.5 O.D. 60° | .929 | 15° |

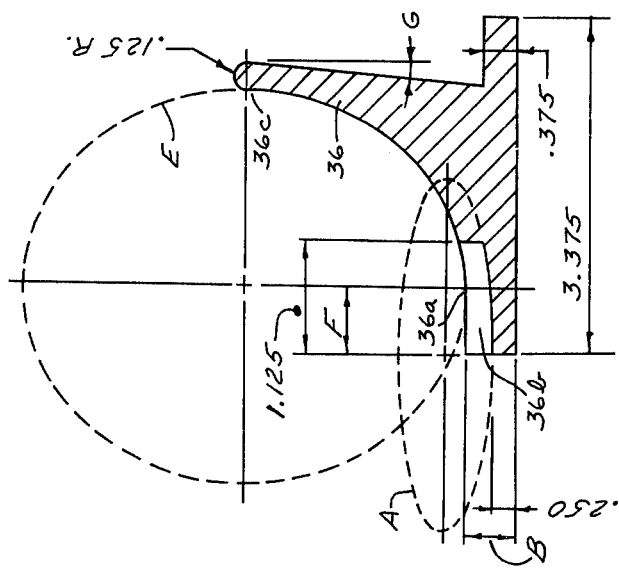
FIG. 18-D
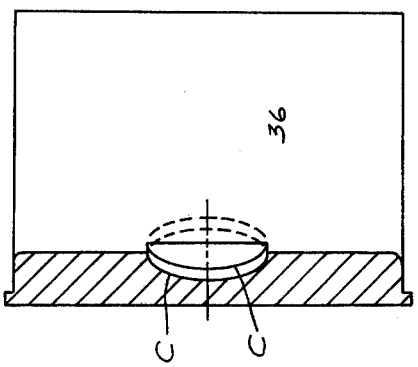
FIG. 18-E
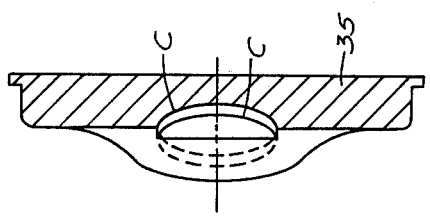
FIG. 18-B
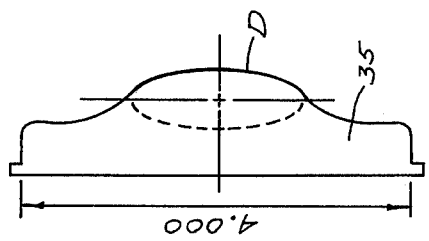
FIG. 18-C
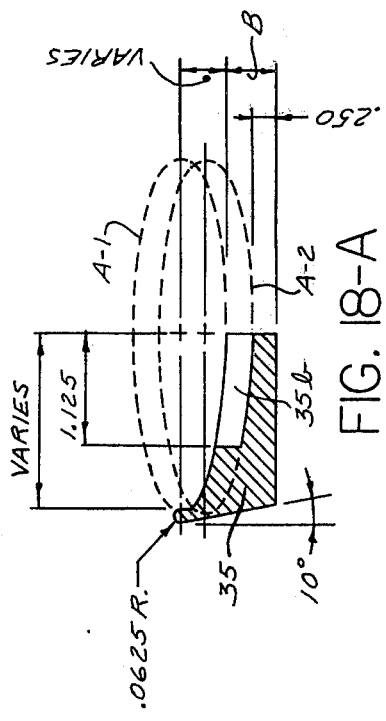
FIG. 18-A

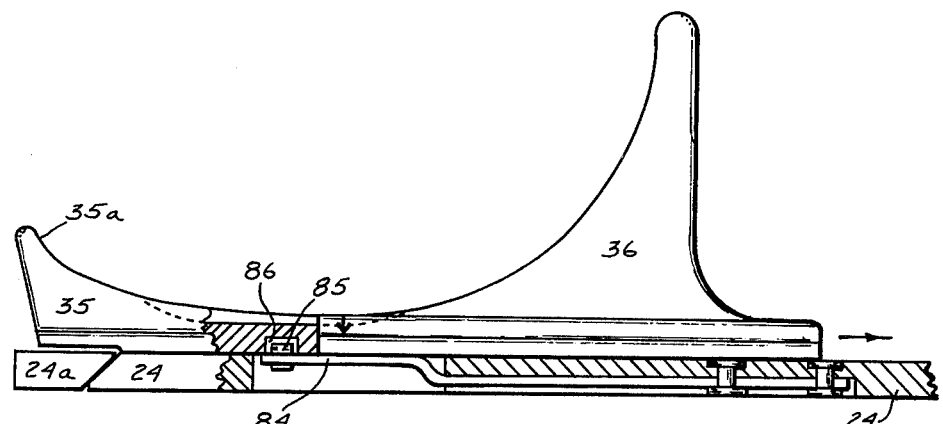
FIG. 19-A
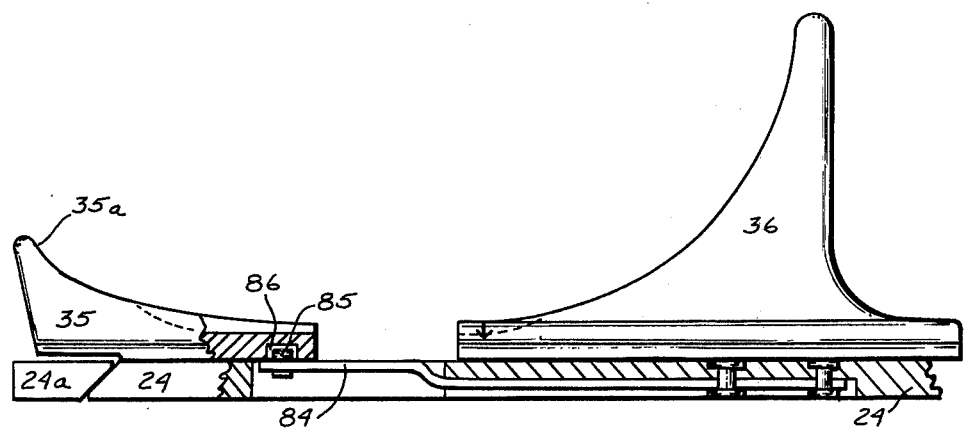
FIG. 19-B
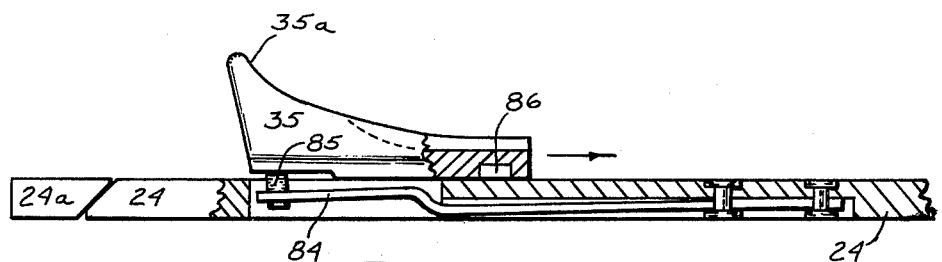
FIG. 19-C

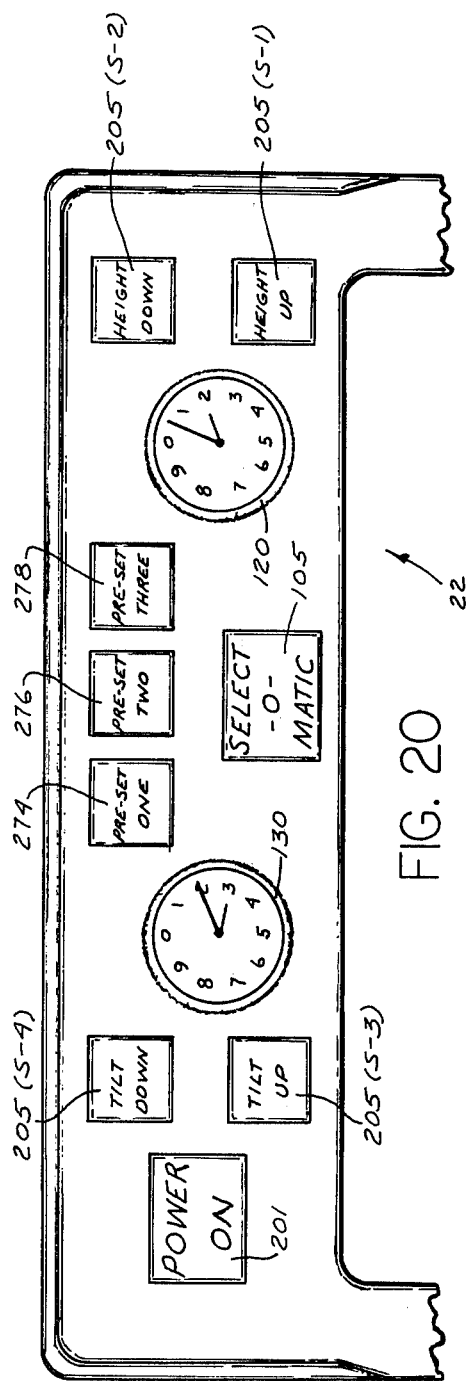
FIG. 20
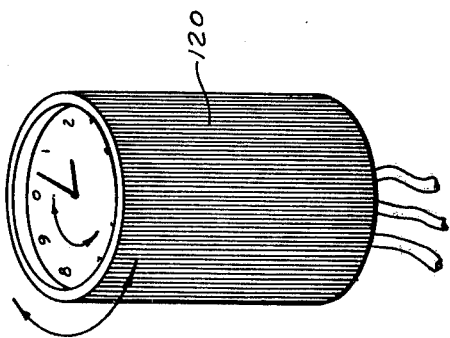
FIG. 20-B
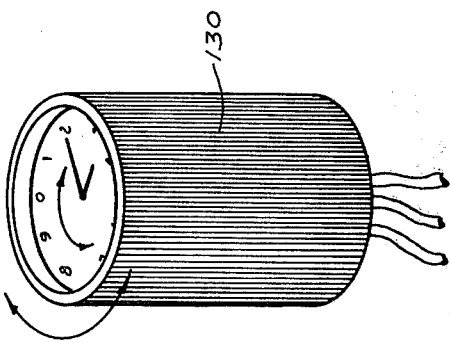
FIG. 20-A

CERVICAL SIDE POSTURE TABLE HAVING EFFECTIVE HEAD RESTRAINT MEANS

BACKGROUND OF THE INVENTION

Chiropractors and other practitioners of the healing arts have for many years utilized various forms of tables upon which patients may lie at the time certain manipulative treatments are to be administered by the doctor. Some of these tables have utilized a movable cushioned headrest portion designed exclusively for upper-cervical treatment, with adjustments and movements of these headrests being in such an appropriate manner as to aid the chiropractor in the administration of such maniuplative treatments.

Adjustment procedures of this type originated Palmer College of Chiropractic, 1000 Brady Street, Davenport, Io. 52803 and these have been used extensively as the main procedure for alleviating major subluxations of the human spine. However, quite unfortunately, many patients in the past have experienced discomfort and pain resulting from the administration of this upper-cervical type of chiropractic treatment.

A number of persons, including several patentees, have developed a variety of cervical side-posture tables in an effort to provide the Doctor of Chiropractic a means for correcting subluxations in the upper region of the human cervical spine. When such movable headrest portion of the table is at precisely an optimum relationship and position with regard to a given patient's head and neck configuration, the chances of the upper cervical vertebra properly receiving the doctor's carefully controlled and properly directed adjusting thrust or force are greatly enhanced. However, for a variety of reasons, such prior art tables have not been nearly as successful as had been hoped.

Major factors contributing to the adverse responses involve the close physical relationship of the atlas vertebra to important neurological structures where this vertebra articulates with the underside of the cranium floor, and the importance of this area of the spline in determining and controlling the proper position of the remaining vertebra and in the prevention of the distortion of the spine with such conditions as scoliosis and kyphosis cannot be overestimated. Therefore, the finite position of the atlas vertebra is very sensitively associated with the patient's total feelings and symptons. Even when a subluxation and/or fixation exist at other points outside of the uppercervical spine area, a concomitant subluxation of the atlas vertebra also seem to almost always exist, as if adhering to a general rule.

Most of the prior art chiropractic tables have exhibited at least some recognition of a basic problem the chiropractor confronts when applying specifically directed thrusts, for these thrusts result in a tendency of the cranium to rock, tilt or otherwise move at precisely the wrong time during the adjustive treatment. This relatively uncontrolled condition of the cranium is quite undesirable, and almost invariably leads to an unstisfactory response or adverse reaction, or considerable discomfort if not pain. It is to overcome shortcomings on the part of prior art devices insofar as properly immobilizing the head that have resulted in our designing an entirely new immobilization arrangement that is quite effective and entirely painless.

Another problem involed with the use of prior art devices has been the considerable amount of time and effort that the chiropractor must expend in positioning the headrest to the proper attitude preparatory to the adjustment procedure, both initially and on return visits. Even with the practice of the present invention there will be a great need for the chiropractor to carefully move the headrest to an optimum position, both from the height as well as the tilt standpoints, at the time of any patient's visit. To this end, we have provided a highly effective control arrangement involving push buttons, selected ones of which the chiropractor need only depress in an appropriate manner in order to bring about needed fine grain movements of the headrest in both height and tilt.

Still another shortcoming of prior art devices has been the fact that in utilizing ordinary procedures, it has not always been conveniently and expeditiously possible for the chiropractor to position the adjustable headrest for a given patient in the same precise position it was in during that patient's previous visit or visits. Considerable time was typically utilized in initially finding the optimum position for the headrest, and usually a similar amount of time is spent in the same endeavor on that patient's return visit, and as a result, many doctors are dissuaded from putting forth sufficient headrest positioning efforts on behalf of each and every patient.

Accordingly, it is a primary object of this invention to provide a very precise and accurate control arrangement for positioning the movable headrest of a chiropractic table, such that upon the chiropractor achieving a proper headrest position from both the height and tilt standpoint for a given patient, these positions can be ascertained electronically and thereafter automatically and accurately returned to at the time of each return visit by that patient, with such able to be accomplished by the expenditure of minimal efforts by the chiropractor.

SUMMARY OF THE INVENTION

Initial revelations of certain portions of this invention to the U.S. Patent Office were made in Disclosure Documents 036304 and 038157, dated Oct. 24, 1974 and Jan. 27, 1975, respectively.

In accordance with this invention, we have provided a chiropractic table having a movable headrest portion, with the arrangement being such that by placing the patient's head thereon, the chiropractor can expeditiously and painlessly secure his or her head in a position that is optimum from the standpoint of the adjusting procedure that is about to be undertaken.

Our novel headrest is advantageously configured in such a way that the chiropractor can select from a variety of mix-matchable two piece sets of mastoid and cephalic supports, and mount on the headrest, that pair of supports that he has ascertained to be of appropriate size and configuration for a given patient.

Selected elevational and tilt movements of the headrest portion of my novel table are now brought about as needed, and in order to accomplish same, the chiropractor needs only to manipulate selected push buttons and controls on the control panel in an appropriate manner.

At such time as the chiropractor has thus completed the task of disposing the headrest in the appropriate position for this patient from the standpoints of height and tilt, he then temporarily secures the patient's head on the headrest by the use of restraint means. Temporary immobilization of the head is completed by swinging a specially-configured yoke from an out-of-the-way position, into a position essentially over the patient's head. At that time, the chiropractor rotates an associated adjustable knob of a restraint assembly associated with the yoke. The restraint assembly has a multi-pad arrangement, which is caused by knob rotation to be advanced downwardly, into direct and firm contact with the cranium portion of the patient's head. By selective rotation of the knob and by certain feedbacks as to pressure applied by the knob, the chiropractor is enabled to apply just the proper amount of pressure to the patient's cranium as to adequately immobilize it, and hold it securely. The mastoid support of the aforementioned two piece mastoid-cephalic assembly principally serves to react the force applied to the head by the restraint assembly of the yoke. Then, further in accordance with my invention, we provide additional restraint means serving to prevent my rolling of the head during the adjustment procedure. This latter is brought about by the provision of facial and occipital restaining members, which are moved againts the front and back portions of the face and head, respectively, with these members being secured in the optimum position by the chiropractor before commencing treatment.

Considerable skill on the part of the doctor is necessary beyond this point, and accordingly, the powered system we use is designed to make possible the desired slow and fine grain movements necessary for accurately positioning the headrest. Thereafter, he proceeds to administer thrusts to certain selected ones of the patient's neck vertebrae, with his hands applied in the manner as generally taught in chiropractic colleges. We have found that patients almost universally agree that a treatment on our table is generally much more effective than a treatment on any known prior art device, which devices do not utilize a proper immobilizing head restraint device, nor offer positive mastoid support through the headrest.

Subsequent to the administration of the adjustment thrust(s), by means of which the proper position of the atlas has een re-established and corrected with respect to the immobilized cranium, the yoke is swung out of the way, thus allowing the patient to rise. Importantly, however, before the headrest is moved in any way from the position found to be optimum for this patient, we proceed to energize a particular control circuit on the control panel associated with the headrest. This circuit entails the use of a pair of helical potentiometers, one being utilized in height circuit, and the other being utilized in the tilt circuit. During this particular operating mode, the control buttons previously used for height and tilt movements are caused to become illuminated, or more particularly, one of the height changing buttons, and one of the tilt changing buttons, are caused to become illuminated. By the chiropractor (or his assistant) then carefully making selective rotational adjustments of the helical potentiometers, an electrical position representing a simulation of the height and tilt positions found appropriate for the patient just treated can be established and recorded on the patient's record for future reference.

It is to be noted that an electrical balance exists when both buttons associated with height adjustments, and both buttons associated with tilt adjustments are caused to become illuminated. This is a balance of voltages between the helical potentiometers on the control panel, and potentioeters associated with the height and tilt drive mechanisms of the headrest assembly. Numbers indicated on the faces of the helical potentiometers represent values that can be recorded as the specific height and tilt of the headrest platform appropriate for a given patient. These values can be programmed back into the helical potentiometers on this patient's future visits, thus causing the headrest assembly to accurately return to the precise height and tilt positions previously found to be most appropriate.

We have found that chiropractors previously unacquainted with the use of a table having a headrest assembly that can be automatically positioned, readily adapt to the procedure we utilize, involving the use of helical potentiometers and selectively illuminated push buttons, by the use of which the chiropractor can rapidly yet accurately ascertain the precise locations of height and tilt appropriate for the patient on his table.

The helical potentiometers we prefer are devices having a form of clockface thereon, with hands to tell the precise rotational adjustment that the chiropractor has found to be appropriate. However, digital readout devices having identical functions are just as acceptable. Other forms of readout may be accpetable, but we try to avoid arragements that are too sophisticated or expensive.

With our invention, a chiropractor will be able to effectively and readily treat existing problems in the upper-cervical spine that may cause the manifestation of symptoms at other points in his body. There appears to be a causative relationship of the problems which exist outside of this upper-cervical spine area with spinal problems which are present in the spinal column below the level of the primary scoliosis (which is an abnormmal lateral curvature of the spine), with the possible exception of such bone structural formations and malformations as are congenital. We have found that in most instances, the patient is almost entirely oblivious to the importance or relationship of these upper-cervical spine problems with his symptoms.

For example, in the case of acute or chronic sciatica, it is often the tendency of many practitioners to treat on the merit system, which is treatment at or near the exit location from the spine of the affected nerves, and, in this case, the sciatic nerve as well as associated nerves would be treated. Such treatments might well entail manipulation, heat, traction or the like. However, by understanding the relationship of the apparently dormant upper-cervical spine conditions to the lower spine problems where the symptoms are manifest, the practitioner can in many instances bring about a dramatic relief by first correcting the upper-cervical spine conditions. Following the procedure we describe herein will in many if not most instances bring about an appropriate alteration in the lower spine conditions at the merit zone level, that previously could not be satisfactorily treated at the local merit zone level only. Thus, by our procedure, the steps necessary to gain a more permanent and lasting relief for the patient are taken.

Generally speaking, human beings begin to manifest ill-health symptoms following a prolonged period of unsuspecting nerve interference and neurological stress, apparently initiated as a result of a gradual breakdown and deterioration of the normal integrity of the spinal column. This dis-ease process may be brought about as a result of an accident, fall, or the like, which causes injury to the spine and its associated structures. The prolonged use of a bed having inadequate support, and/or the general wear and tear during the course of routine living may on the other hand be the cause of spinal difficulties. In any event, an overall observation will show this breakdown and deterioration condition of the spine to manifest with an observable scoliosis upon X-ray examination, which may have spread the entire length of the spine. This dis-ease process appears to be traceable as initiating in the cervical spine or, more specifically, in the upper-cervical spine area, with a subluxation also invariably being present in the uppermost cervical spine articulations. It is to be noted that the late Bartlett Joshua Palmer, D.C., Ph.C., who was a major developer of the chiropractic phillosphy, science and art, firmly established during his life's work the importance of the proper care of this upper-cervical spine subluxation condition.

Our invention enables the chiropractor to properly and adequately position any given patient in an appropriate manner as to physically straighten, reduce and relieve by placement techniques the stresses of the aforementioned uppermost scoliosis condition in the upper portion of the cervical spine, such being accomplished by the advantageous use of our novel headrest, with its selective height and tilt capabilities. It is further to be noted that the use of our device makes it possible to reduce and relieve the stresses induced by the scoliosis condition, such being accomplished by the proper shoulder placement of the patient, prior to the administering of the adjustic thrusts used to correct the existing subluxation condition. This appropriate corrective adjustment or treatment in the upper-cervical spine area not only relieves the subluxation condition, but also causes an improvement in the stance and integrity of the uppermost scoliosis condition, which should be labeled for clarification purposes as the primary scoliosis (which always involves at least the area of the intervertebral disc between the second and third cervical vertebrae), and with this immediate aforementioned improvement causing in turn a proportionate improvement in each successive compensatory scoliosis below, thereby eliciting a gradual straightening of the entire spinal column by a chain reaction type event and causing the spinal clumn to return toward its more normal stature and integrity. This, in turn, reduces the nerve stress and interference which is responsible for a multitude of spine-related disease processes in humans. Repetition and refinement of this entire procedure on subsequent follow-up office visits allows the chiropractor to correct or at least relieve these undesirable and detrimental health problems with which all humans have to contend as a result of the everyday stresses of life.

As the chiropractor enlarges his knowledge of the human spine, and improves his skill, he will find that the immobilizing headrest restraint device in accordance with our invention will be an invaluable tool and aid in helping to achieve desired objectives. These objectives are, of course, to achieve corrections that have been heretofore impossible to satisfactorily and completely accomplish, inasmuch as prior art devices provided no effective means for immobilizing the essentially spherically shaped head of the patient, nor did they provide a genuinely positive mastoid support to aid the chiropractor while he or she was endeavoring to adjust the atlas. Unfortunately, the typical adjusting forces of the chiropractor, when applied to the atlas vertebra, encourages the cranium to rock, roll or otherwise tilt in some manner. Any such motion is quite adverse and detracts considerably from the ultimate correction the chiropractor is endeavoring to achieve in the cervical spine area. It is the prevention of such motion that is basic to our invention, and the highly effective device we have envolved makes it possible, for the first time, for a chiropractor to effect satisfactory change in the general as well as the specific neurological stresses of the patient. When this has been accomplished, the patient's overall health and happiness will be dramatically improved.

It is therefore a primary object of this invention to provide a novel side-posture table of extremely sturdy construction for use by chiropractors and other practitioners, as will enable certain specific adjustments to be most effectively made upon a patient.

It is another important object of this invention to provide a cervical side-posture table having novel restraint means thereon, by use of which the doctor can painlessly yet effectively immobilize a patient's head, thus maximizing the efficacy of the adjustive treatment.

It is yet another object of this invention to provide a novel headrest having specifically designed support and restraint members thereon, including a mastoid support for engaging a lower portion of the mastoid bone of the patient, as well as a padded member designed to contact the upper and lateral portions of the patient's head, and at the latter location apply a controlled force serving to cause the patient's head to tightly fit against the mastoid support, thus to minimize any tendency of the head to rock or tilt during the treatment period.

It is still another object of this invention to provide a novel mastoid support usable in conjunction with an adjacent cephalic support, with optimally sized ones of these components able to be selected and installed on a supporting headrest by the doctor at the time he commences the treatment of a given patient.

It is yet still another object of this invention to utilize a pair of novel facial-occipital supports whose position with respect to a patient can be independently established, with these supports functioning in concert with other support components in minimizing a rolling type motion of the patient's head on the headrest of our table.

Another object of this invention is to provide a novel headrest assembly for a side-posture table, capable of being moved for selected distances in the height direction, thus making it possible to dispose the vertebral members located between the upper-cervical and the mid-cervical spine of the patient in the most appropriate configuration from the standpoints of his or her condition of vertebral displacement and the type of adjustic remedy to be applied.

It is another object of this invention to provide a table having a novel headrest portion capable of tilting movements independent of height movements, thus simplifying the task of the chiropractor in causing the position of the novel mastoid support of the headrest to be in the optimal position with respect to the mastoid bone of the patient.

It is another object of this invention to provide a headrest portion that is movable laterally with respect to the longitudinal centerline of the machine during the time a patient's head is restrained, thus to cause the relationship of head and upper cervical spine to be optimized with respect to his torso.

It is another object of this invention to provide a powered control unit for enabling selected height and tilt movements of the headrest to be accomplished merely by the selective manipulation of push buttons by the doctor, thus enabling him to put his full attention on the effect of the height and tilt changes to the patient.

It is another object of this invention to provide automatically functioning height and tilt control means for the headrest of the table, such that upon the programming of certain information pertinent to a known patient into the control means, the headrest can be caused to move rapidly and accurately to the position previously ascertained to be optimal for this patient.

BRIEF DESCRIPTION OF FIGURES OF DRAWINGS

FIG. 2 is a plan view of the headrest portion of this machine, showing further details of the support and restraint components, as well as the control panel;

FIG. 3 is a side elevational view showing the headrest portion disposed at approximately the same height as the flat surface of the table, and further showing the yoke member in approximately an operational position;

FIG. 4 is a fragmentary side elevational view showing, by the use of phantom lines, a raised position of our novel headrest;

FIG. 5 is another fragmentary side elevational view showing various positions of tilt that the headrest portion may be easily moved to;

FIG. 6 is a side elevational view to a larger scale, with certain portions cut away to reveal the components principally responsible for bringing about selected height and tilt motions of the novel headrest;

FIG. 7 is a view taken along lines 7—7 in FIG. 6, so as to further reveal the components employed for bringing about movements of the headrest assembly in height and tilt;

FIG. 7A is a view to a much larger scale of the potentiometer arrangement utilized to provide an indication of the actual height of the headrest;

FIG. 7B is a view to a much larger scale of the potentiometer arrangement utilized to provide an indication of the degree of tilt to which the headrest has been moved;

FIG. 7C is a perspective view of the support means for the tilt actuator, shown to a much smaller scale;

FIG. 8 is a view illustrating the relationship of the movable yoke with respect to the mastoid and cephalic supports, with the full line position of the yoke being an out-of-the-way position, and the dashed line position being a typical operational position;

Figure 15:
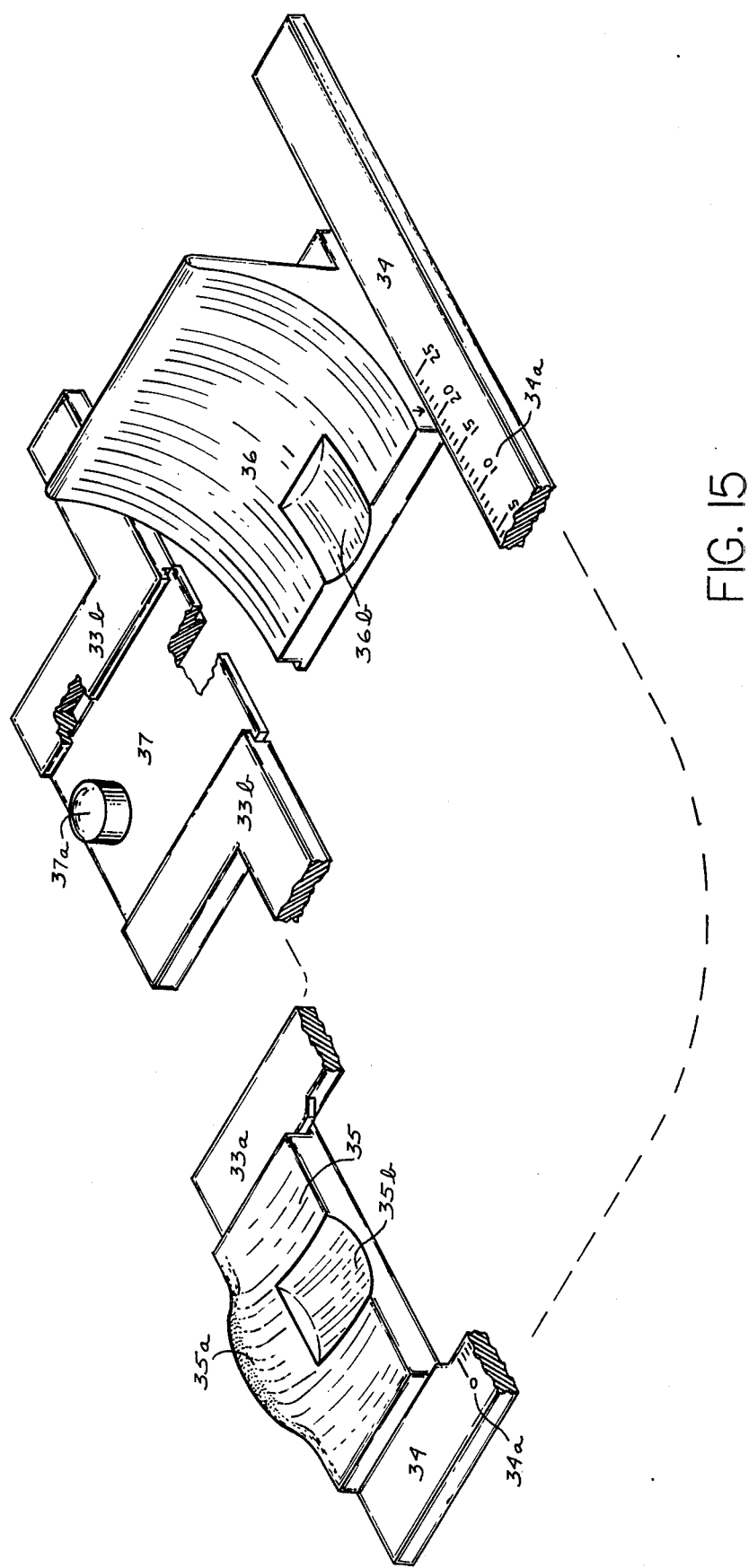
Figure 16:
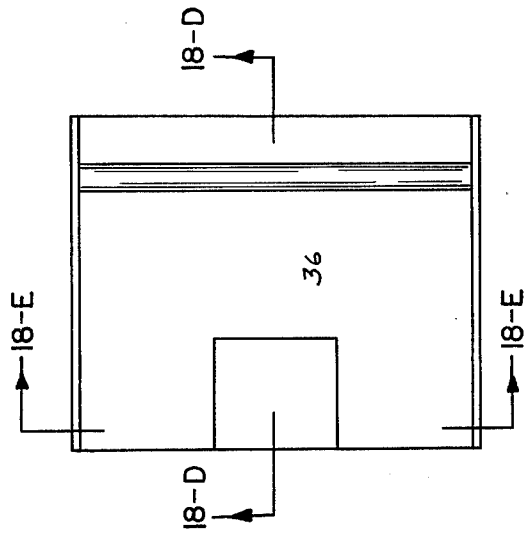
Figure 17:
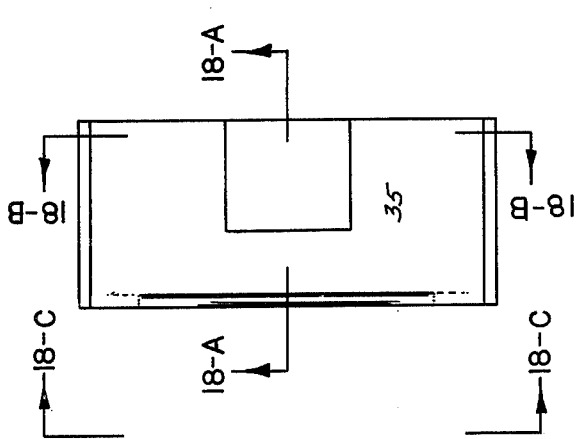
Figure 21:
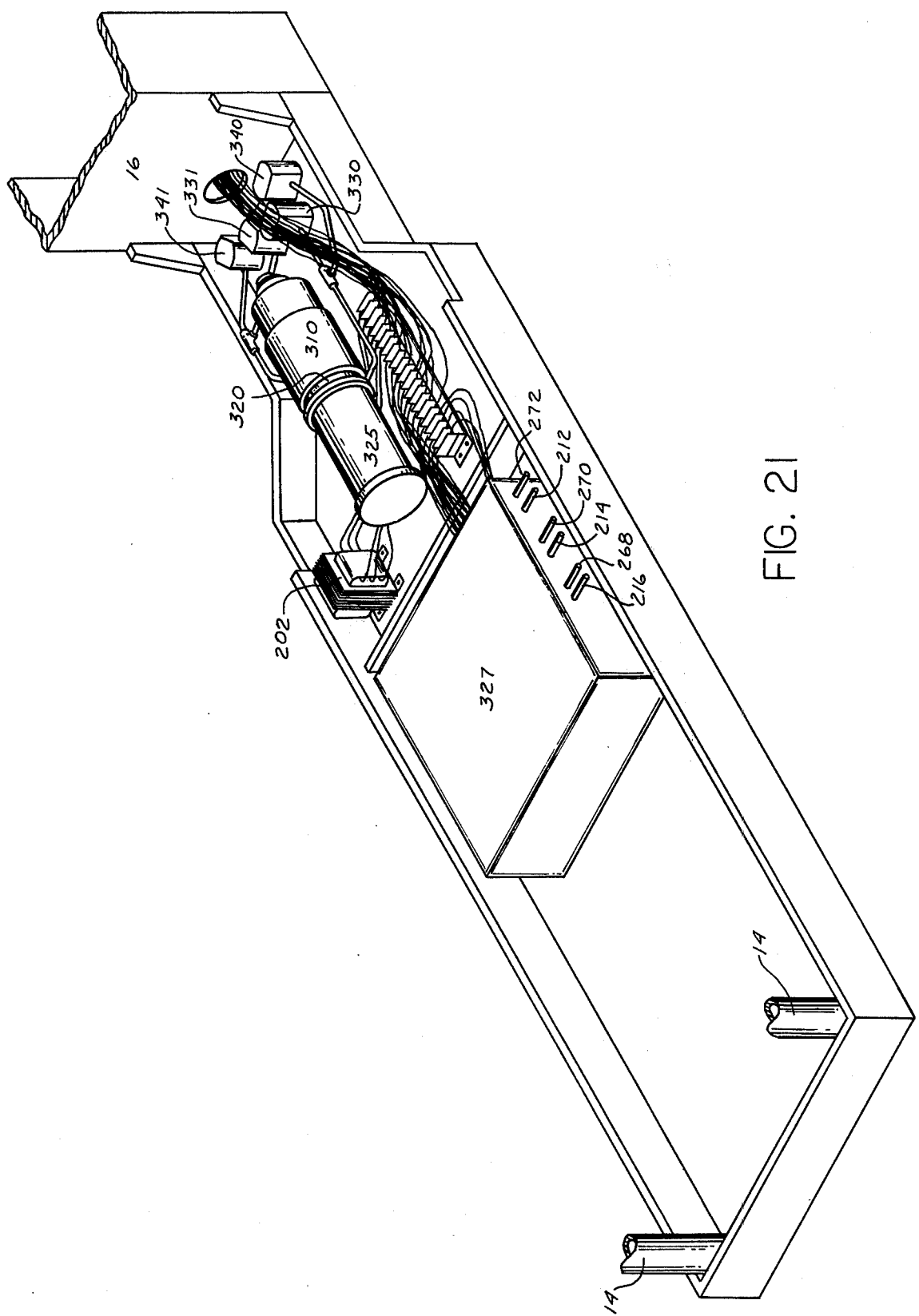
Figure 22:
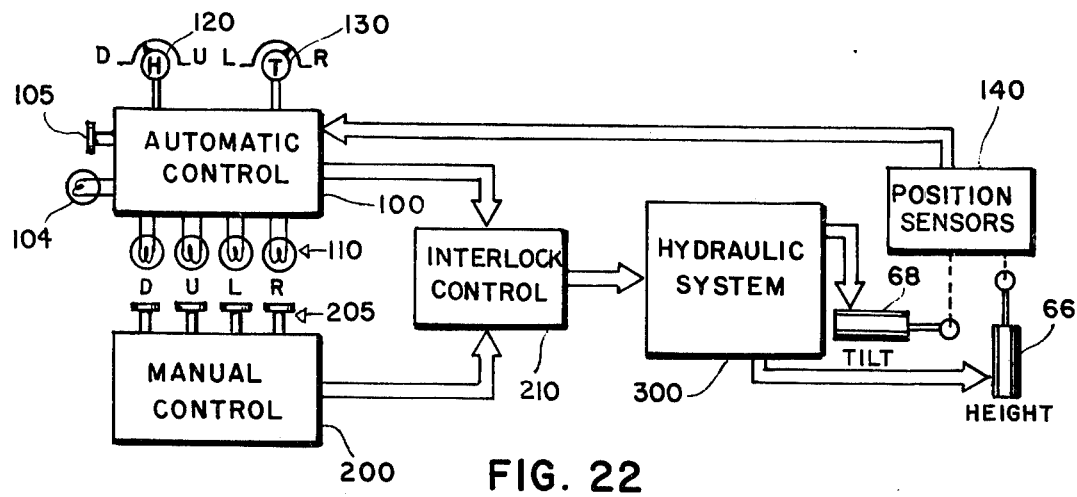
Figure 23:
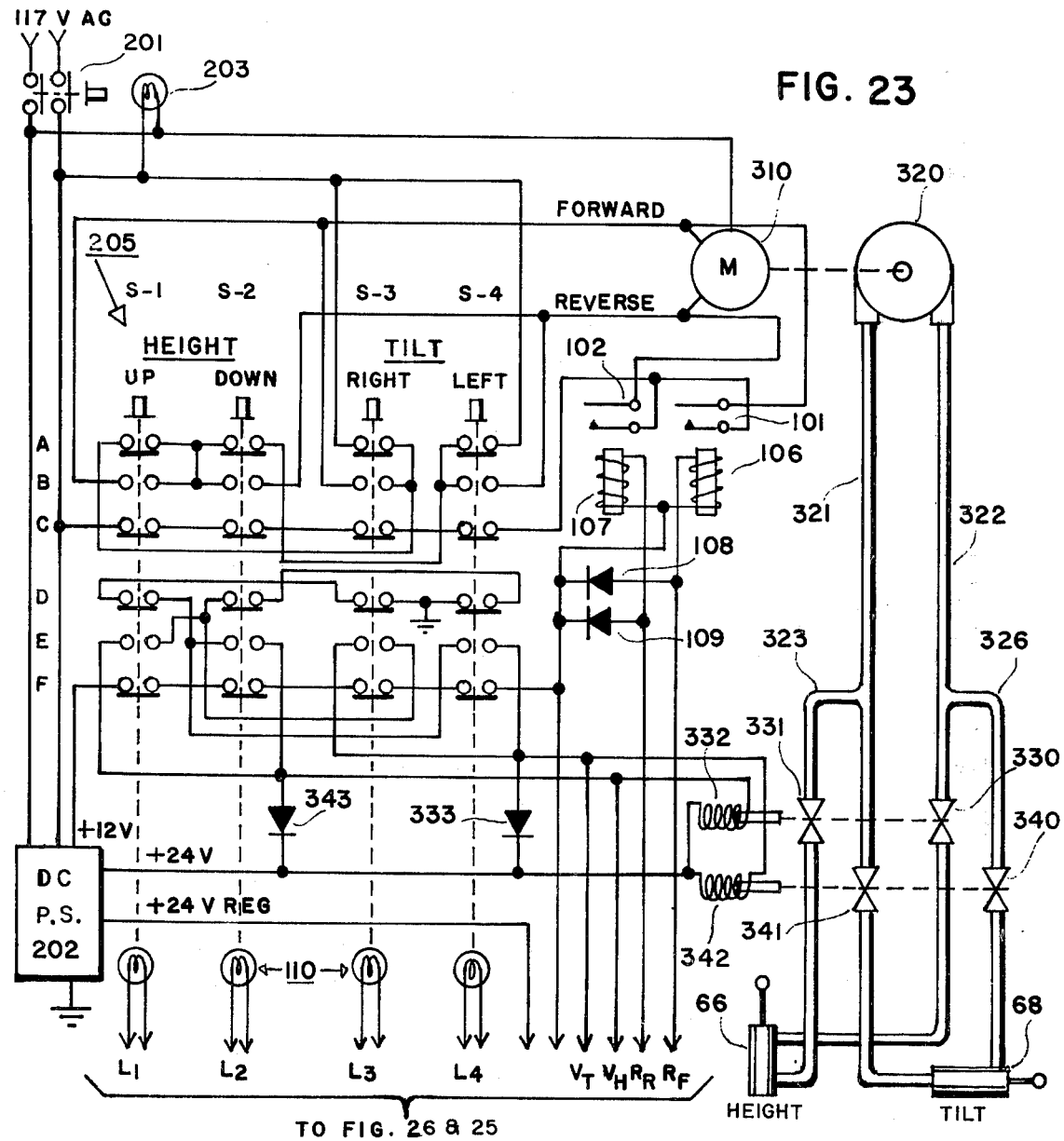
Figure 24:
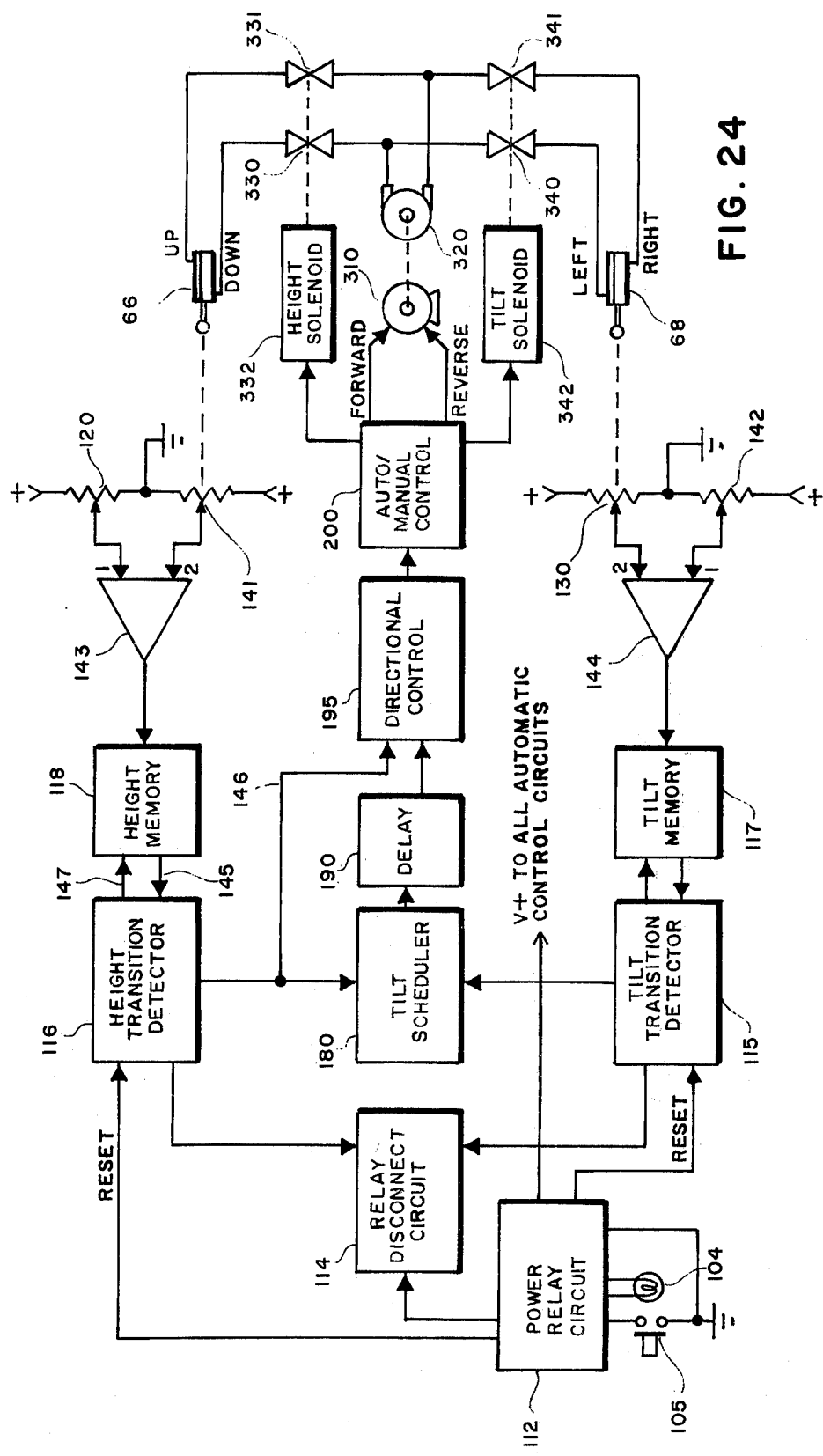
Figure 25:
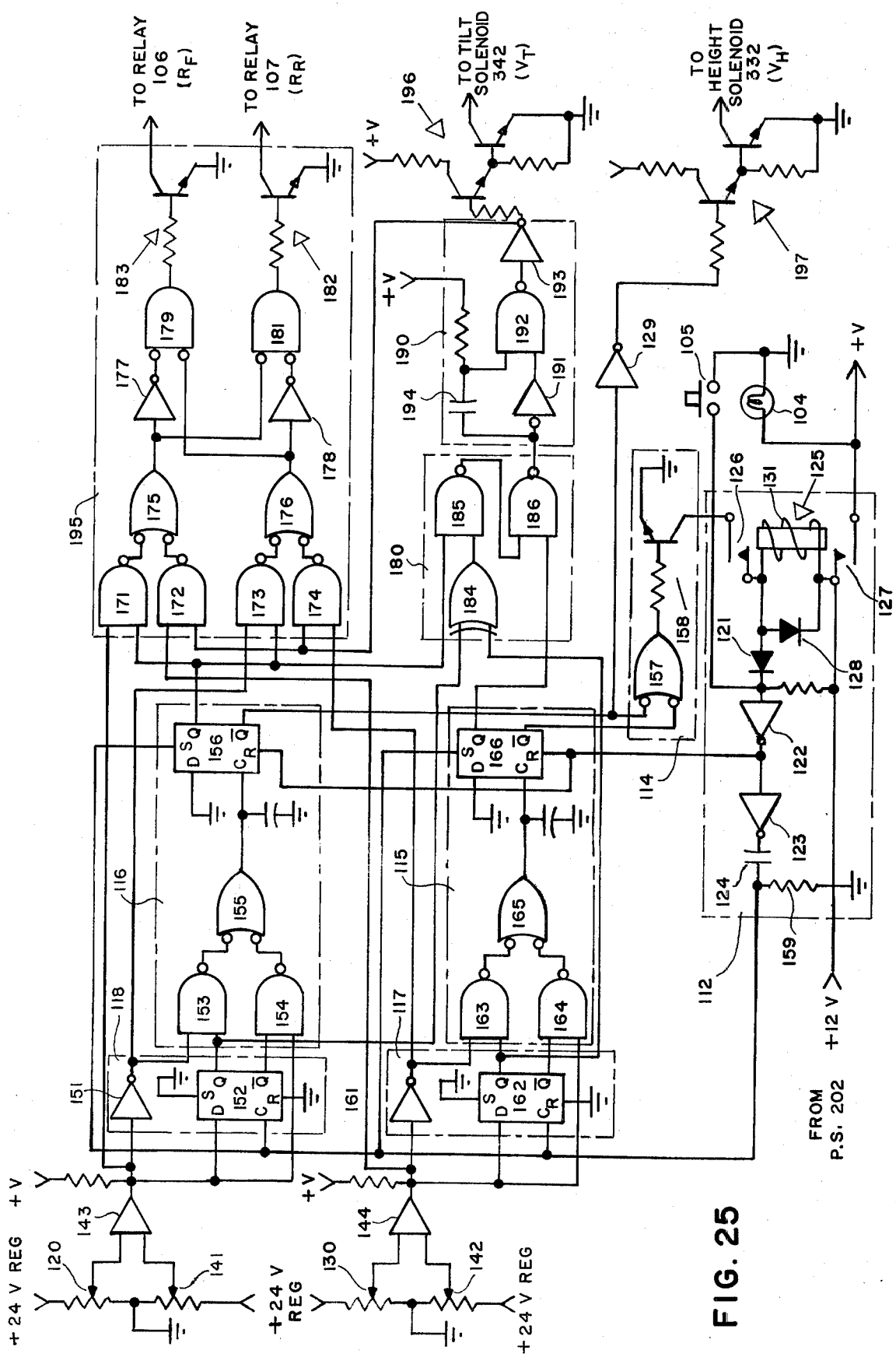
Figure 26:
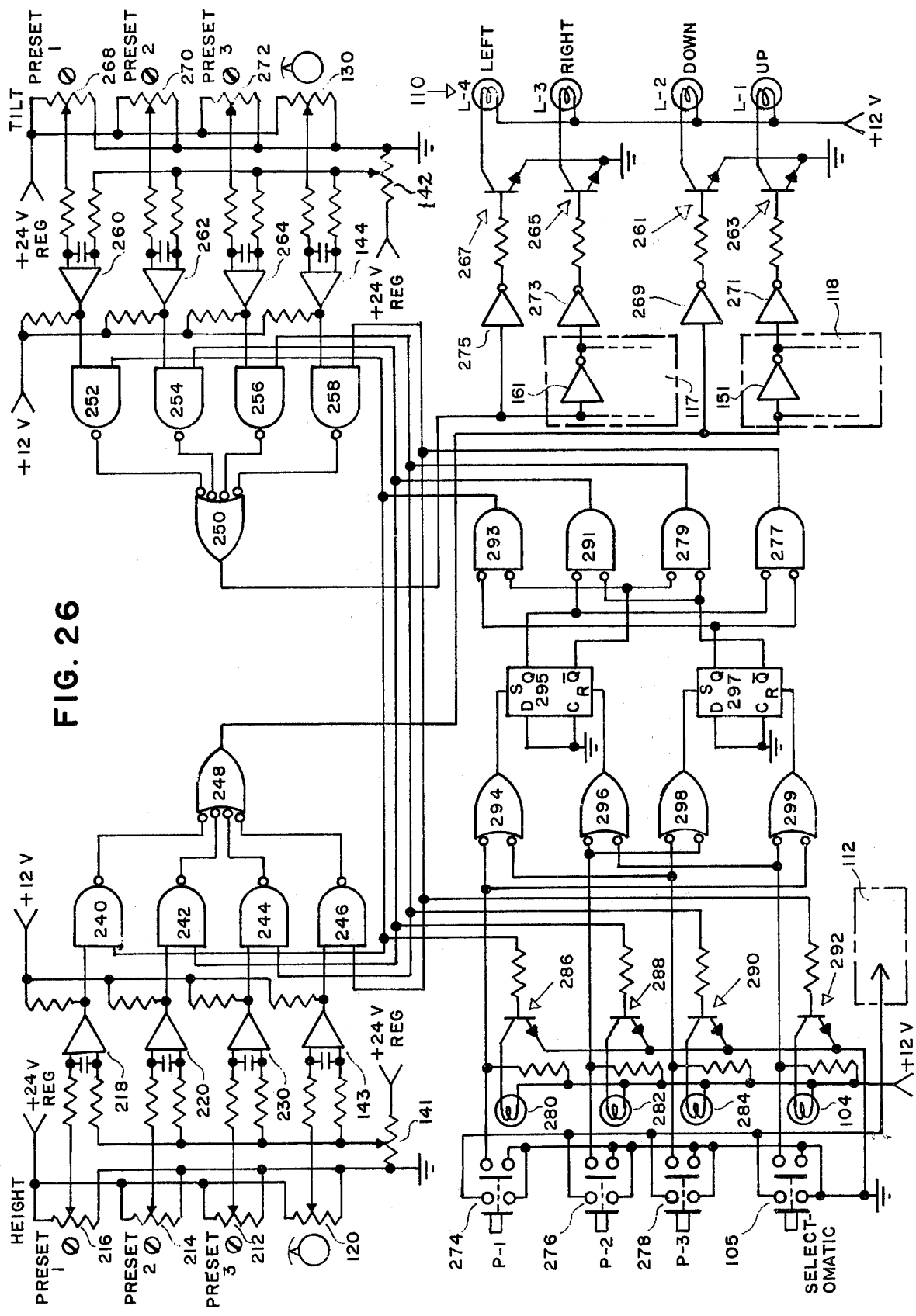

FIG. 9 is a view of the yoke member in an active, head-contacting position, with arrows showing how the force applied by the yoke to the patient's head is reacted by the novel mastoid member provided in accordance with this invention, and with this figure further showing the appearance of a normal upper and midcervical vertebral arrangement, which is to be contrasted with certain abnormal relationships of these vertebral members that are also illustrated;

FIG. 10 is a fragmentary view of the upper portion of the yoke as well as the tripod member supported by the yoke, with this view illustrating various positions to which the tripod member is movable in accommodating various head sizes;

FIG. 11 is a fragmentary view showing the manner in which a head-contacting pad is movable with respect to the arm of the tripod on which it is mounted;

FIG. 12 is a plan view of our novel headrest arrangement, showing the operative relationships of the mastoid and cephalic supports to the tracks in which they are mounted, as well as the facial-occipital supports and the yoke and tripod members;

FIG. 13 is a side elevational view easily relatable to FIG. 12, and taken from the rear of the mastoid support in order to reveal the interrelationship of this support member to the trackways of the baseplate, as well as the means for accomplishing lateral movements of the baseplate;

FIG. 13A is a view of a typical facial-occipital support, with this member being sectionalized so as to reveal the construction making it possible for the head-contacting portion to be moved rapidly under some circumstances, and with fine grain movements under other circumstances;

FIG. 14 is a view to a much larger scale of the knob used on the yoke member for making height adjustments of the tripod member, with these components being sectionalized to reveal internal construction;

FIG. 15 is an essentially perspective view of our novel mastoid and cephalic supports in position in the track members in which they are operatively disposed, with the track members in this instance being cut and moved to essentially orthogonal positions so as to dispose the head-contacting portions of the mastoid and cephalic supports in the attitude in which they may be viewed;

FIG. 16 is a plan view of the mastoid support and the cephalic support in an approximately normal operating relationship, with various cutting planes being indicated on these supports in order that certain important cross-sectional views may be referenced;

FIG. 17 is a chart setting forth with respect to the mastoid and cephalic supports the ellipses that are used in the manufacture of four or five different sizes of mastoid and cephalic supports, with this chart therefore providing the specific information that is associated with the configuration of each such member;

FIG. 18A is a cross-sectional view taken along the longitudinal centerline of the mastoid support, with certain ellipses being superimposed on this figure, that can be correlatd with the chart of FIG. 17;

FIG. 18B is a sectional view of the mastoid support, taken along lines 18B—18B in FIG. 16, with this view showing a pair of small ellipses that may be regarded as described a recessed area to receive the anti-helix portion of the ear;

FIG. 18C is a view of the edge of the mastoid support that is farthest from the cephalic support, with this view illustrating the fact that only the center portion of this edge of the mastoid support is raised to form the upwardly projecting contoured lip;

FIG. 18D is a cross-sectional view taken along the longitudinal centerline of the cephalic support, with certain ellipses being somewhat superimposed on this figure that can be correlated with the chart of FIG. 17;

FIG. 18E is a view of the edge of the cephalic support taken aong lines 18E—18E in FIG. 16 in order to reveal the edge nearest the mastoid support, with this view showing a pair of small ellipses that may be regarded as described a recessed area for the anti-helix portion of the ear;

FIG. 19A is a view showing the mastoid support and the cephalic support in contiguous positions, which is the position in which these components would be located if the head being supported is comparatively small and round, with portions of the matoid support and baseplate being cut away to reveal internal construction;

FIG. 19B is a view showing the cephalic support in a position moved away from the mastoid support, which is the condition that obtains when the head that is being supported is comparatively large;

FIG. 19C is a view in which the mastoid support has been moved away, as indicated by an arrow, from the position in which it is locked in placed by a spring-biased member;

FIG. 20 is a plan view of the novel control panel that is utilized on the forwardmost edge of the headrest support platform, with certain push buttons and other control means on the control panel being provided such that the doctor can selectively bring about desired height and tilt adjustments of the headrest;

FIG. 20A is a view to a much larger scale of the helical potentiometer associated with tilt;

FIG. 20B is a view to a much larger scale of the helical potentiometer associated with height changes;

FIG. 21 is a view of the underside of our machine, illustrating certain principal components associated with the selective positioning of the movable headrest portion, including motor, hydraulic pump, hydraulic reservoir, electronic control unit, and the solenoid control valves, the latter being used to assure that the movable headrest portion will not tend to drift or slip away from a selected position;

FIG. 22 is a simplified block diagram of the control system preferably employed for operating our new cervical side-posture table;

FIG. 23 is a schematic of the manual control arrangement and certain aspect of the interlock control function;

FIG. 24 is a simplified block diagram showing the basic elements of the automatic control circuit we utilize;

FIG. 25 is a schematic of the principal elements of automatic control circuits arranged in an operational manner; and FIG. 26 is a schematic diagram of the electronic circuits utilized with the present functions of our inventions and also illustrates the indicator lamp circuits used in a calibrating regime in the operation of this invention.

GENERAL DESCRIPTION

Figure 1:
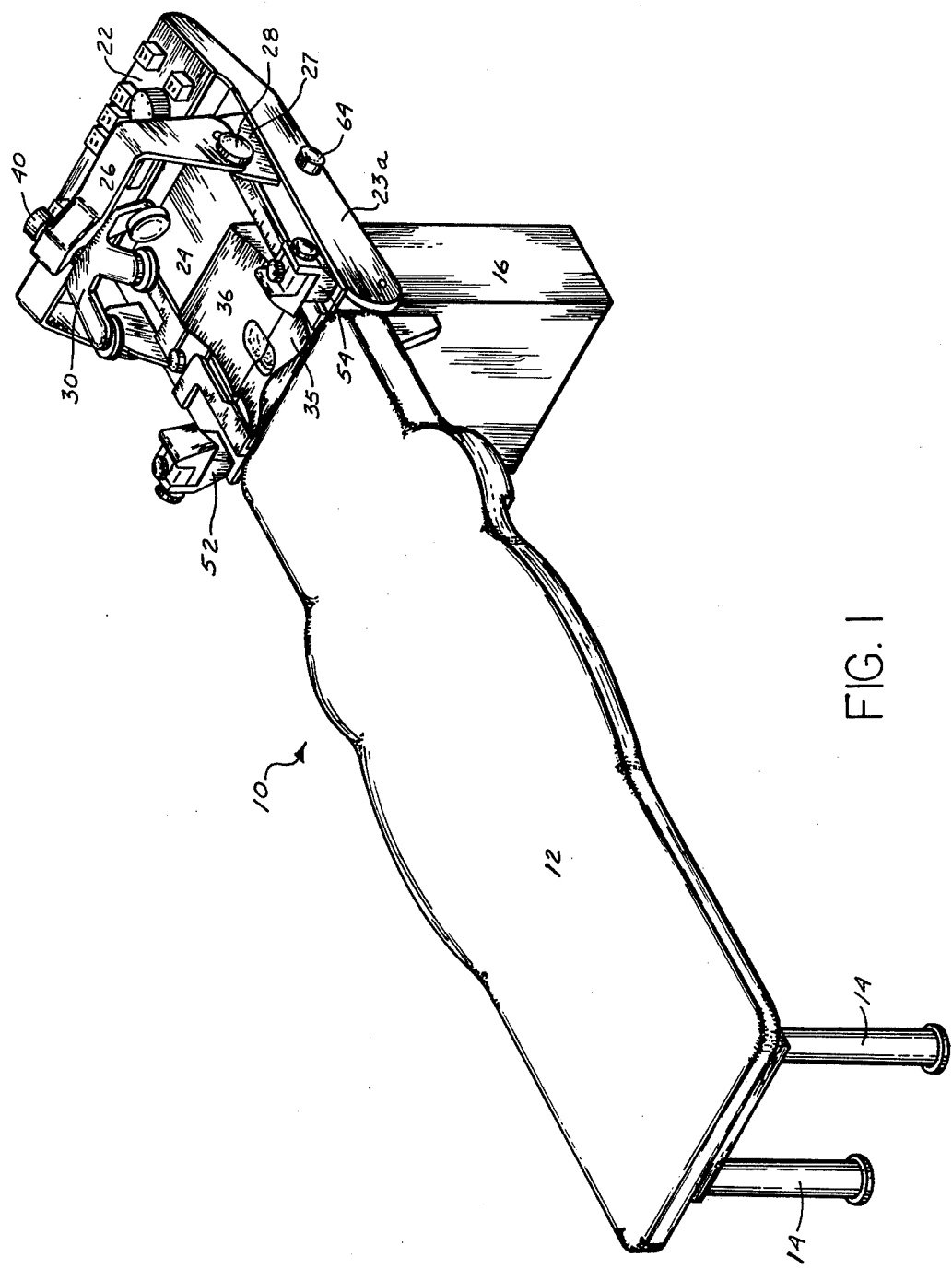
FIG. 1 is an overall perspective view of our side-posture table, revealing the portion upon which a patient lies, as well as the movable headrest portion and its several means for supporting and immobilizing a patient's head.

Turning to FIG. 1, it is there to be seen that we have shown a cervical side-posture table 10 in accordance with our invention, involving an elongate cushioned upper surface 12 to receive the torso and legs of a patient, with legs 14 being used on the underside of the table for supporting the portion opposite the head end.

The head end of the table is supported by a vertically disposed housing 16, in the interior of which are certain power-operated components 18, hereinafter discussed, for the selective elevation and tilting of the headrest assembly 20. These height and tilt changes of the headrest assembly are brought about as a result of the selective manipulation of the appropriate buttons of the control panel 22, visible in FIGS. 1 and 2 as well as in other figures. The construction of the control panel will be discussed at length hereinafter.

In accordance with a preferred embodiment of this invention, the headrest assembly 20 is movable heightwise, as shown in FIG. 4, as well as in tilt, as shown in FIG. 5. These movements are made possible by the use of hydraulic actuators visible in FIGS. 3 through 7, whose construction and operation will subsequently be discussed at length.

In order that the headrest assembly will have the requisite strength, we utilize a headrest support platform 23 principally involving a casting, such as of aluminum, that extends from a hinge point adjacent to the head end of the surface 12, to the forwardmost portion of the headrest assembly, where it supports the control panel 22. The casting is preferably somewhat U-shaped in cross-section, as revealed in FIGS. 7 and 13, thus to define side members 23a and 23b that effectively resist torsion and bending during operation and use of this device.

FIGS. 6 and 7 reveal the manner in which the headrest support platform 23 is supported, which is by the use of a laterally extending structural member 25, affixed at the upper end of the movable rod portion 72 of the actuator 66 concerned with height movements of the headrest assembly. The structural member or crosshead 25 is of a length as to fit between the side members 23a and 23b of the headrest support platform, with a pair of pins 25a serving as a pivotal interconnection between the member 25 and the platform 23. The inner ends of these pins threadedly engage the ends of the member 25, with the outer ends of the pins having smooth surfaces so as to minimize friction, and make rotational movements of the platform 23 about this hinge point relatively easy to accomplish.

An essentially flat plate, hereinafter referred to as the baseplate 24, is slidably mounted upon the platform 23, with the baseplate serving as the mounting means for all of the head supporting and cradling devices hereinafter described. Inasmuch as it is desirable for the baseplate to be laterally movable on the platform 23 (that is, movable toward side member 23a or side member 23b as they appear in FIG. 13), we bevel the front and rear edges of the baseplate, so as to enable it to slidably fit between front and rear gibs attached to the headrest support platform 23 by the use of screws. Rear gib 24a is visible in FIGS. 19A through 19C, but front gib is not depicted in the drawings.

In order to enable the operator to be able to selectively bring about lateral movements of the baseplate and the components supported thereby, we weld or otherwise secure a threaded boss 62 on the underside of the baseplate 24, which boss is slidably disposed in lateral slot lateralslot 63 located in the platform 23. An elongate rod 60, of a length sufficient to extend between the side members 23a and 23b, is rotatably mounted in these members, which rod has a threaded midportion. As will be noted In FIG. 13, the midportion of the rod 60 threadedly engages the boss 62, with this arrangement enabling rotations of the rod to bring about lateral movements of the baseplate 24 in its gib trackways. We provide a knob 64 on each end of the rod 60, thus to enable the chiropractor, by rotating the knobs, to easily achieve appropriate lateral adjustments of the baseplate with respect to the headrest support platform, as is frequently necessary during treatment of a patient.

As will become more apparent as the description proceeds, it is important to painlessly yet effectively restrain a patient's head against unwanted movement during the treatment of the patient's disorders. To that end, we provide mastoid and cephalic supports 35 and 36, respectively, upon which the patient's head rests, as well as a yoke member 26, supported by members 27 disposed on opposite sides of the baseplate 24, as best seen in FIGS. 1, 3 and 8. The yoke 26 is of generally inverted U-shape, with it to be understood that the yoke is in a position above the patient's head, as shown in FIG. 9 when the patient's head is to restrained on the headrest assembly, and in the position shown in full lines in FIG. 8 when not in use, which means that it is swung to a position in the vicinity of the control panel 22. Pins 27a on the members 27 pivotally support the yoke, and we use a pair of tightening knobs 28 for securing the lower ends of the yoke 26 in the desired position on the support members 27, with these knobs having threaded portions thereon which threadedly engage tapped holes in the support members 27. Circularly-shaped slots are provided adjacent the support points of the arms of the yoke, so as to permit movements of the yoke through a wide arc. Thus, when the patient's head is positioned on the headrest assembly in the manner to be described hereinafter, the yoke 26 can be moved to an operative position above the patient's head and then the knobs 28 tightened in order to hold the yoke in the chosen position. Supported in a central portion of the yoke in the manner illustrated in FIGS. 1 through 3, 8 and 9 is a tripod member 30, with a pad 32 disposed at the lower end of each of its three legs. These pads 32 are for contacting the patient's head for the purpose of restraining same after the head has been placed in the proper position on the mastoid and cephalic support assembly.

As will be noted in FIGS. 12 and 13, the mastoid and cephalic supports are slidably mounted on the longitudinal centerline of the baseplate, with tracks 33 and 34 being utilized so as to assure that these supports will not become displaced laterally. These components are removably mounted on the baseplate 24 with track members 33 and 34 being employed for this purpose. The track members are disposed on either side of the centerline of the baseplate, with the spacing of the tracks being such that the mastoid and cephalic supports can be accommodated in the manner shown in FIG. 12. Thus, the chiropractor is able to choose the mastoid and cephalic supports appropriate for a given patient, which supports are able to accommodate the head of the patient properly, whether he be lying on his right side or his left side. The mastoid-cephalic supports are a particularly important aspect of our invention, and will hereinafter be discussed in considerable detail.

POWERED MOVEMENTS OF HEADREST ASSEMBLY

Referring to FIGS. 3 through 7, it is to be seen that the power-operated components 18 concerned with raising or lowering the headrest assembly principally involve double-acting hydraulic actuator 66 operationally arranged to provide vertical movements, and double-acting hydraulic actuator 68 arranged to provide tilting type movements to the headrest.

Although a motion-providing system employing gears could have been used, this would have permitted certain amounts of backlash to have been introduced into the system, which would have been quite undesirable. Not only is backlash non-existent in the hydraulic system we employ, but also this arrangement permits normally-closed solenoid valves to be used in the lines to the hydraulic actuators, which in effect enable the headrest assembly to be locked in the chosen positions of height and tilt. In this way, any tendency of the motion-providing means to drift is eliminated, thus providing the operator with a very solid under-support for the headrest components, as is vital if the desired movement of the atlas vertebra with respect to the occipital portion of the cranium is to be successfully brought about.

As best revealed in FIGS. 6 and 7, the double-acting hydraulic actuator 66 concerned with vertical movements of the headrest assembly is secured to the bottom of the housing 16 by means of a pin or bolt 67, which fits into a clevis arrangement. A piston rod 72 extends upwardly from the actuator, with the upper end of the piston rod being connected to the previously-mentioned crosshead member 25. Quite obviously, as the piston (not shown) that is disposed in the cylinder of actuator 66 is caused to move upwardly or downwardly by the selective porting of hydraulic fluid below or above the piston, the piston rod 72 along with the member 25 are caused to move up or down, depending of course on the porting in a given instance.

Affixed to the underside of the member 25 are the upper ends of a pair of slidable, elongate structural members 78 that are approximately equidistant from, and parallel to, the piston rod 72. The lower ends of these column-like members 78 are secured to a vertically movable U-shaped platform 80, best seen in FIG. 7C. This platform is U-shaped in order to provide appropriate clearance for the cylinder 66, and forms a mounting clevis for actuator 68, to which the lower end of this actuator is secured by means of a pin or bolt 69. As is apparent, as the actuator 66 causes the member 25 to move up or down, this in turn causes the member 80, as well as the lower portion of the actuator 68, to undertake like movements. Because of this height changes effected by actuator 66 do not change the tilt of platform 23.

Stability for the arrangement just described is provided by members 82 that form a non-movable upper portion of the housing 16, for, in the members 82, the structural members 78 are slidable. Since all of these members are of comparatively rugged construction, the movable headrest assembly is supported at the end of the table in a very sturdy manner.

As to be seen in FIG. 7, the pins 25a are utilized at each end of the member 25, with these pins forming a support for the side members 23a and 23b of the headrest support platform 23, used to support the baseplate 24. Because the only contact between the hydraulic acuator 66 and the headrest support platform is through these pins, tilting movements of platform 23 can be brought about in a manner to be described hereinafter, without the lifting arrangement causing any interference therewith.

Extending upwardly from the actuator 68 is a piston rod 74. The upper end of the piston rod is provided with a fitting that enables it to be affixed to a clevis on the underside of headrest support platform 23. A clevis pin 75 is used for this purpose and, as shown in FIG. 6, the pin 75 is several inches away from the pins 25a, so, as a consequence, movements of the piston rod 74 outwardly from the cylinder 68 bring about upward tilt of the headrest support platform, whereas inward movements of this piston rod bring about downward tilt of platform 23. Pin type joints are of course used at both end of actuator 68 in order to prevent binding or interference.

As should now be apparent, the chiropractor can bring about tilting movements of the baseplate 24 by selectively energizing the hydraulic actuator 68 in such a manner that its rod 74 will move in a direction to bring about the desired tilt.

As should now be obvious, height movements of the platform 23 as a result of the energizing of actuator 66 do not affect tilt, and tilting movements of the platform brought about by the energization of actuator 68 result in angular changes of the baseplate but they do not basically change the height thereof. This is to say, height and tilt movements are independent of each other, although a common supply of hydraulic fluid is used, and the controls for the one are adjacent to the controls for the other.

As previously mentioned, FIG. 4 reveals how the supplying of hydraulic fluid to the underside of the piston contained in actuator 66 (not seen) brings about a raising of the platform member but no change in tilt thereof, whereas FIG. 5 reveals for a given position of the piston rod 72 of the actuator 66 that tilting movements of the baseplate 24 can be brought about by the selective porting of the field above or below the piston contained in actuator 68.

It is of concern to the chiropractor that the headrest support platform 23 and the baseplate 24 have no tendency to drift either from the height standpoint or the tilt standpoint during use, as mentioned hereinbefore, so as illustrated in FIG. 21, we provide two pairs of solenoid-operated valves, with valves 331 and 330 being in the hydraulic lines concerned with height changes of the headrest support platform, and valves 341 and 340 being disposed in the hydraulic lines concerned with tilt changes of this platform. Such solenoid valves are electrically actuated to the open position only during the time it is desired to bring about deliberate height or tilt movements of the baseplate. At all other times these valves are closed, and, as a result, great stability of the platform 23 and the baseplate 24 in the chosen position is achieved.

In FIGS. 6 and 7, rack 70 may be seen to extend between structural members 25 and 80, and therefore moves in a vertical direction with movements of platform 23. Rack 70 drives a potentiometer 141 through a suitable pinion attached thereto; note FIG. 7A. Potentiometer 141 serves to produce a DC voltage whose value is directly proportional to the height of the baseplate 24. As will be described in detail hereinafter, this voltage is used in the automatic operation of our headrest assembly. A similar potentiometer 142 is shown in FIG. 7 attached to member 25 and coupled to gear segment 71; note FIG. 7B. Gear segment 71 is attached to the medial side of member 23b of the platform 23. Therefore, relative motion between platform 23 and crosshead member 25 as baseplate 24 is tilted will cause rotation of potentiometer 142, producing a DC voltage proportioned to the degree of tilt. This is also used in the automatic operation of our headrest assembly, as will be explained hereinafter.

THE YOKE ASSEMBLY

It has previously been described how the yoke member 26 is supported from the pair of upstanding members 27 that are disposed on the sides of the baseplate 24, with the knobs 28 being provided so that by the twisting of same in the tightening direction, the chiropractor can be assured that the yoke will stay above the patient's head, in a desired angular position with respect to the baseplate.

Supported from the underside of the yoke 26 at a location directly above the longitudinal centerline of the mastoid and cephalic supports is tripod 30, each leg of which is equipped with a pad 32 that can be brought into firm yet comfortable contact with the patient's head, in order that the head can be held against the mastoid and cephalic supports 35 and 36 in a desirable way. It is of course necessary from patient to patient to adjust the height relationship between the tripod member 30 and the yoke, and such is made possible by the appropriate manipulation of a height adjustment knob 40 disposed above the yoke member, as revealed in FIGS. 8 through 10.

Referring to FIG. 14, it is to be seen that an enlarged portion 41 of the knob 40 is disposed so as to be easily grasped by the fingers of the operator. Directly below the portion 41 are screw threads 42 that are threadedly received in an appropriate aperture in the center portion of the yoke member 26. Also from this figure it is to be noted that this portion of the knob member is hollow and contains a cylindrical member 44. It is desirable for the tripod member to be non-rotating with respect to the yoke member, so to that end we provide a lateral extension 46 on the lower end of the cylindrical member 44, with an upstanding pin 48 being disposed at the outer end of the extension 46. The pin 48 is of such a diameter as to be easily received in a hole 49 disposed on the underside of the yoke, with this arrangement therefore, being such that the cylindrical portion 44 cannot rotate within the threaded portion as the operator is caused the rotation of the threaded portion 42 of the knob in a desired direction with respect to the yoke.

Affixed on the lower side of the cylindrical portion 44 is a gimbal member 50, with the tripod member 30 being supported from the member 50 in such a way as to be swung freely for a limited number of degrees. This arrangement is of course provided in order to permit the tripod member to accommodate heads of various sizes and configurations, with movements of the yoke member with respect to the gimbal being necessary in order to properly accommodate each next patient on the table. The gimbal member is non-rotating, for the pin 48 assures that the tripod member will always be in a desired and proper orientation with respect to the head of the patient with which it is used. Because of the arrangement thus far described, it should be obvious that as the height adjustment knob 40 is rotated by the chiropractor in the tightening direction, the pads 32 are caused to move in the direction of contact with the patient's head, whereas opposite rotation of the knob moves the pads away from such contact.

MASTOID AND CEPHALIC SUPPORTS

The mastoid support 35 and the cephalic support 36 are contoured components designed to provide a close, comfortable yet firm support for the head of a patient to be treated. As will be noted from several of the figures, including FIG. 15, the mastoid support 35 is provided with an ear recess 35b, and the cephalic support is provided with an ear recess 36b. These recesses come into substantial alignment ith each other when the supports are moved close together, such as shown in FIGS. 1 and 12, with the purpose of these recesses being to receive the ear when the patient lies on his side, thus eliminating any tendency for the ear to be mashed or compressed.

The mastoid and cephalic supports are preferably made from lightweight base material, such as of aluminum or plastic, and contoured in the manner shown in FIG. 15, with the base material being covered at the upper surfaces with a material such as rubber ⅛ to 3/16 inch thick, of a durometer hardness of 70 to 80. In that way, each of these supports is quite comfortable insofor as the patient is concerned, yet serves to hold the head of the patient in a firm manner, as is important during the time the doctor is making the desired adjustment.

It is particularly important that the mastoid support 35 be contoured to fit closely around the mastoid bone of the patient's head, as shown in FIG. 9, for the mastoid support is principally responsible for reacting the force created when the doctor tightens the knob 40 of the yoke. In connection with FIG. 9 is should be noted that the mastoid and cephalic supports may on certain occasions be disposed closely together as shown in this figure, but it is more typical for these supports to be disposed somewhat apart. The various vertebral arrangements shown in FIG. 9 will be discussed at greater length hereinafter.

Inasmuch as the sizes and shapes of patients' heads vary widely, it is desirable not to limit the chiropractor to a single pair of mastoid and cephalic supports but, rather, to provide him an assortment of sizes from which he can select these supports most nearly fitting a given patient's head. Since it is of importance to be able to secure the mastoid support firmly to the baseplate 24, and to be able to adjust the position of the cephalic support with respect to the mastoid support until such time as the patient's head is properly received, we provide track members disposed upon the baseplate in the manner shown in FIG. 12, and we provide suitable mounting bases on the mastoid supports and the cephalic supports so that selected ones of these can be locked in desired operational positions.

The preferred track arrangement involves a left track member made up of sections 33a and 33b, and right track member 34, the latter being a continuous member. Inasmuch as it is desired for the mastoid and cephalic supports to reside on the longitudinal centerline of the baseplate 24, we secure the principal portion of the track members on the baseplate at locations equidistant from the centerline, as revealed in FIGS. 12 and 13, utilizing screws or the like for such purpose.

Certain of the figures of drawing, such as FIGS. 12, 13 and 15, reveal that we provide a flanged edge on each side of the base of each mastoid and cephalic support, so that these members cannot be easily dislodged from proper engagement with the track members. Correspondingly, we configure the track members so as to have edge portions that overhang the flanged edges, with this type construction being clearly revealed in FIG. 13.

Although the left and right track members are in essentially parallel relation, the track members are configured so as to define a somewhat narrowed portion at the location where the mastoid support 35 is, to be retained. This arrangement is revealed in FIG. 12, and it is pertinent to reiterate that the mastoid support selected for a given patient has but a single operational position, which may be observed in FIGS. 19A and 19B.

On the other hand, the track members are spaced a bit wider apart at the location where athe selected cephalic suppot is to be retained in position, with FIG. 12 revealing this construction. The cephalic support selected for a given patient may be secured in the track members at any of a wide range of operating positions, with the means we prefer to use for this purpose being a slidable locking member 37. The member 37 is mounted in orthogonal portions of track members 33b and 33b, so as to enable it to be moved either toward or away from the near edge of the cephalic support member 36. We prefer to dispose a cam (not shown) on the underside of member 37, with the rotational position of the cam being determined by the rotation of a knob 37a on the upper surface of member 37. Left or right movement of the slidable locking member 37 is determined by the direction the doctor choose to rotate the knob 37a.

As is obvious, the doctor locks the selected cephalic support between the track portions 33b and 34 at the location appropriate for the patient, this locking action being achieved by rotating the knob 37a in the proper direction unitl the edge of the locking member 37 presses tightly against the near edge of the cephalic support, locking it tightly in the selected position. The doctor is expected to enter into the personal history he keeps on each patient, an identification of the mastoid and cephalic supports he found appropriate in each instance. We provide a scale 34a along the track member 34, as is to be seen in FIGS. 12 and 15, thus to enable the doctor to adequately describe the precise location of the cephalic support be found to be correct. A meansuring marker is to be noted on the side of the cephalic support in FIG. 15.

It should be apparent from the table of FIG. 17 that we provide the doctor with a selection of several mastoid supports and several cephalic supports that are of varying sequential size, any one pair of which can be installed on the trackways 33 and 34, inasmuch as the base portions of the supports are of consistent, uniform size. Having made the selection, he slips the chosen mastoid section into and between the narrowed section of the parallel portions of the tracks 33a and 34, sliding this mastoid portion into the track in a direction away from the control panel. He simultaneously depresses the flat spring 84 disposed on the underside of the baseplate 24, until such time as the lower edge of the mastoid support has cleared the upstanding pin 85 mounted on spring 84. See FIGS. 19A through 19C. He then continues to slide the mastoid support until such time as the pin 85 has snapped into a hold 86 provided on the bottom of the mastoid support, this of course resulting from the fact that the spring biases the pin upwardly. This will now cause the mastoid support to be held in an appropriate opertional position until such time as it is desirable that the chiropractor wish to remove this mastoid portion, and replace it with another size mastoid portion that may be determined to be more appropriate for the next patient to be treated.

Removal is accomplished simple by the reversal of the installation procedure, which would be to first depress the spring 84 to withdraw the restraining pin 85 from the small hole 86 on the underside of the mastoid support, and slide the support 35 in a direction toward the control panel 22 until it has cleared the tracks.

Next, the chiropractor selects an appropriate cephalic section from a series of available mix-matchable sections, and places the best of this section on the baseplate 24, between the widened portion of the tracks 33b and 34. It was previously noted that the track 34 has a retaining lip under which to receive a widened portion of the cephalic section's base. This portion of track 33b has no such lip, but rather utilizes the slidable locking member 37, which can be moved against the cephalic section with sufficient force as to hold it firmly against the track 34. By following the proper procedure, the chiropractor can select the mastoid and cephalic supports appropriate for each patient and can then find the best position for the cephalic portion by sliding it along its track, essentially on a trial-and-error basis, until such time as it has properly contacted the upper and lateral portions of the patient's cranium, when the patient is properly placed and ready to receive treatment. The chiropractor then locks the cephalic section into its final position for this patient by manipulating the knob 37a, as previously described.

Following this, the yoke 26 is swung from an out-of the-way position into a position essentially over and in direct contact with the patient's head and cranium, as previously described, with this being followed by all the essential procedures for set-up and immobilization preparatory to the treatment. Quite important insofar as the mastoid and cephalic supports are concerned, at the conclusion of the treatment, after the patient has arisen, but before the cephalic section is moved, the chiropractor simply makes note on the patient's record of the exact position of the cephalic support in relation to the scale 34a, for this information can be easily referred to and utilized for rapid set-up on future office visits of this particular patient.

Turning now to FIGS. 16 through 18, it is to be seen that certain information is there set forth as to the specific configuration of mastoid and cephalic supports available for the chiropractor to select from during his treatment of a patient. Although the configurations described in these figures are the most useful, it should also be obvious that other mastoid and cephalic support configurations could be used without deviating from the spirit and scope of this invention.

FIG. 16 reveals plan views of the mastoid and cephalic supports and indicates the locations of the various cutting planes utilized in the creation of FIGS 18A through 18E. FIG. 17 is a table that has been prepared with regard to several ellipses, including a near circle, and several dimensions utilized in configuring the various support members, with it to be noted that suppot sizes Baby through Extra Large are defined.

Certain of the column headings, such as A, C and D, indicate the size of ellipses used in arriving at the geometry of the supports, whereas other columns of this table indicate other important information in this regard.

Referring to FIG. 18A, it will be seen that this longitudinal cross section of the mastoid support 35 reveals the use of two somewhat superimposed ellipses in the layout of the head-contacting portion of this member. The major axis of each ellipse extends horizontally, and these axes are spaced apart a short distance, such as one-forth inch. The left-hand end of each ellipse is quite important in serving to define the configuration of the head-contacting portion of the mastoid support. More specifically, the left-hand end of the upper level ellipse A-1 serves to define the principal head-contacting surface of the mastoid support, whereas the lower level ellipse A-2 serves to define the bottom portion of the ear receiving recess 35b.

Reference to FIG. 18B reveals the two comparatively small ellipses C, with the lower portion of the lower ellipse defining the bottom contour of the ear recess 35b to the location nearest the edge adjacent the cephalic support, and the lower portion of the upper ellipse defining the bottom contour of the ear recess 35b at the rear of such recess. FIG. 18A reveals a typical location at which the upper ellipse may be regarded as having been utilized.

It is important to note in FIG. 18A that an upstanding, somewhat hook-shaped portion 35a is defined by the ellipses, and reference to FIG. 18C reveals that this is the central portion of the mastoid support responsible for contacting the mastoid bone of the patient, as best seen in FIG. 9. As is to be seen in FIG. 9, this portion 35a serves to react the force applied by the knob 40 of the yoke, and prevents slippge of the head at the time the doctor applied the adjustic thrusts. The upper portion of the small ellipse D as viewed in FIG. C is preferably used in configuring this part of the mastoid support.

Reference back to FIG. 17 at this point reveals the various sizes of the ellipses A, C and D that may be utilized in creating the sequence of mastoid supports the doctor preferably should have on hand in order to treat patients of a variety of head sizes.

Turning now to the cephalic support 36, it is to be seen in FIG. 18D that we have detrmined the principal head-contacting contour by a 60° ellipse, which is a near circle. Column E sets forth the various sizes of ellipses that may be used in this regard, taking the head size of the patient into consideration. The location of the center of ellipse E with respect to the edge of the cephalic support nearest the mastoid support it determined by the dimension appearing in column F of the table of FIG. 17, whereas the configuration of the ear recess 36b along the longitudinal centerline of the cephalic support is determined by the lower edge of an ellipse A of the proper size.

As in the case of the support 35, an ellipse C determines the configuration of the lower portion of the ear recess 35b in a lateral sense, as shown in FIG. 18E.

With further regard to ellipse curve E, the 60° ellipse was chosen in this instance because in the cases where a constant contact could not be maintained throughout the entire incline of the ellipse curve from the flat plateau level at the lowest point of the circle at the outer tip of the radius of the long axis to the outer tip of the radius of the short axis, namely from point 36a to point 36c of FIG. 18D, then this degree, or one of a higher numerical value such as 70°, would offer at least a two point contact to the cranium at points 36a and 36c, which would offer an adequate amount of support with sufficient cradling as to fulfill the purpose of this particular selected section. It is important to note that the particular manner and orientation or posture of the ellipse curve in the cephalic section as to the specific placement of the long and short axes offers as great an opportunity to constant cradling and/or a two point contact for cradling as can be found to match cranium configurations at this area. It should also be noted that cradling is not as critical upon this portion or section as it is upon the mastoid section 35, because the multi-padded tripod configurated device does not essentially force the cranium upon and in firm contact with this cephalic portion 36 as it does with the mastoid bone upon the mastoid portion of the two-piece mastoid-cephalic support.

Further, it should be pointed out that the horizontal profile lines of the cephalic portion 36 as viewed in FIG. 18D which follow the course of the 60° cllipse curve from point 36a to point 36c are straight lines all the way across the width of the cephalic section, and are not dished or concave as one might assume would be necessary, because in most cases the patient's parietal bone contacts an area on the upper surfaces of this cephalic portion more towards the side at the patient's posterior, and is very infrequently positioned and supported directly centered. This section is also obviously to be used by patients lying on either side as may be deemed necessary according to the specific circumstances of that particular individual's needs. Accordingly, the horizontal profile lines are, of necessity, straight.

Additionally, it is important ot note that the recessed area for the anti-helix portion of the ear lobe is installed into this cephalic section quite similar to the manner in which the recessed or depression area was installed in the mastoid portion of the two-piece mastoid-cephalic supports. When these two portions are brought into close proximity, as will be the case when cradling a somewhat round and bowling ball shaped cranium lacking the slight elongation common with most craniums, then the recessed or depression area of this cephalic section will make up the upper half of the area actually needed to comfortably offer proper displacement for the anti-helix portion of the ear lobe proper. As in the case with elongted craniums, then the natural separation space between the cephalic section and the mastoid section will provide the needed displacement area for this portion of the ear lobe.

It should be pointed out that column F of the chart of FIG. 17 represents a flattened plateau area on the top surface of the cephalic section before initiating at point 36a the upward incline along the 60° ellipse curve, and is essentially determined to be the distance of one-third the radius of the short axis of any given specific cephalic portion therein listed. Also, column B of this chart indicates the lower flat plateau surface from point 36a to the edge nearest the mastoid support to have complimentary surfaces with identical thickness dimensions when butting against matching mastoid portions 35. In the event of mix-matching components, the edge corners and surfaces are chamfered for blending and comfort.

Additionally, it should be noted that regardless of which separate and individual cephalic portion or section is selected as being the most appropriate for any particular patient, the bases thereof on all are identical in shape and size, thereby allowing easy interchangeablility and receptivity by athe retaining tracks mounted on the baseplate 24.

FACIAL-OCCIPITAL SUPPORTS

We have found that despite the fact that the doctor has chosen the correct mastoid support and the correct cephalic support for a given patient and properly installed same in the tracks; has placed the head properly in the supports; has installed the yoke over the patient's head; and tightened the knob 40 for the proper number of turns; that there is still some possibility of the head undertaking a type of rolling motion during certain adjustments by the doctor. To that end, we provide a pair of facial-occipital restraints 52 and 54, as shown in FIGS. 12 and 13, which are mounted upon the baseplate 24. Depending upon the direction the patient is facing, and assuming he is lying on his right side, the movable portion 52a of the restraint 52 is brought into contact with the facial or zygomatic bone at the anterior, and the movable portion 54a is brought into contact with the occiput at the posterior, in this instance. Obviously, the role of the movable portions 52a and 54a is reversed if the patient is lying in the other direction.

Referring to FIG. 13A, it may be seen how the knobs 58a and 58b are utilized in the positioning of the movable portion 54a. The base portion of the member 54 is drilled to receive the horizontally disposed bolt attached to knob 58a, and the movable portion 54a is provided with an oversized bore therein that is in alignment with this bolt. Slidably fitted in this bore is a cylindrically shaped sleeve 59, whose position in the bore can be locked by tightening the knob 58b. The interior of the sleevel 59 is threaded to receive the threaded bolt associated with knob 58a, so when the sleeve has been locked with respect to the bore, rotations of the knob 58a bring about carefully controlled adjustments of the position of the member 54a. On the other hand, when the knob 58b is loosened, this allows the member 54a to move with respect to the sleeve, thus making it possible for the chiropractor to make rapid adjustments as to the position of the surface contacting the head of the patient. Obviously, the chiropractor first makes the gross adustments of the movable member, then tightens the bolt 58b, and then proceeds to make fine grain adjustments by rotation of the knob 58a. Construction of the restraint 52 is identical and need not be set forth.

SPECIFIC PATIENT TREATMENT

FIG. 9 illustrates probably the most important physical relationships involved in the practice of this invention and will now be dealt with at length.

In FIG. 9, the patient may be regarded as lying on his or her right side, thus to place the occipital portion of the cranium on view in this figure. Illustrated in approximately correct relationship to the cranium in this figure is the atlas vertebra, known as C1, as well as the axis vertebra, known as C2. This figure further shows vertebra C3 and C4, with all four of these being in a normal, straight-line relationship, and with the discs there between having normal appearance.

For purposes of explanation, we have shown above these normal vertebra another set of vertebra, C2 through C4, with a bulging or ballooning intervertebral disc also being represented. It is important to note that the intervertebral disc bulging in the manner shown high in FIG. 9 is on the same side of the atlas vertebra which is to be treated. Under these circumstances, the headrest will be positioned comparatively low insofar as a centerline of the neck is concerned, at the time the doctor administers the adjustic thrust(s) to the atlas vertebra. The headrest is utilized in a comparatively low position in this instance in order to assist in the doctor's effort in restoring the atlas vertebra to a normal, properly aligned condition. This is to say, upon the headrest being placed at a height commensurate with the bulging intervertebral disc shown in the upper portion of this figure, the doctor, in applying adjusting thrusts to the atlas, may well be able not only to correct the subluxation of the atlas, but also to cause this misplaced intervertebral disc to return to its normal position. The low positioning of the headrest causes pressure to be applied through the vertebrae to the bulging disc, and the correction forces applied to the atlas by the doctor will quite clearly assist in the return of the disc to the normal position.

Turning now to the condition represented by the three vertebrae in the lower part of FIG. 9, it will be noted that the intervertebral disc is bulging to the side of the patient opposite to the side of the atlas to be treated. Under these circumstances, the doctor causes the headrest to be positioned comparatively high insofar as the centerline of the neck is concerned, at the time the doctor administers the adjustic thrust(s) to the atlas vertebra. The headrest is utilized in a comparatively high position in this instance in order to assist in the doctor's efforts in restoring the atlas to a normal, properly aligned condition. This is to say, upon the headreast being placed at a height commensurate with the bulging intervertebral disc shown in the lower portion of this figure, the doctor, in applying adjusting thrust(s) to the atlas may well be able to correct the subluxation of the atlas, as well as to cause this misplaced intervertebral disc to return to its normal position, as the high positioning of the headrest causes pressure to be applied through the vertebrae to the bulging intervertebral disc, and the correction forces applied to the atlas by the doctor will assist in the return of the disc to the normal position.

It is important to note that the various support components associated with the headrest of our invention effectively resist the adjustic thrust(s) that are applied by the hands of the doctor when they are placed directly above and in contact with the transverse portion of the atlas. In FIG. 9, it will be noted that we have utilized a pair of curved arrows, with the heads of these arrows being placed so as to indicate a tendency toward a counterclockwise motion of the patient's cranium resulting from the application of force to the atlas in the illustrated example. As indicated previously, if motion were to take place in this maner, it would be entirely inconsistent with the overall objective of the treatment to be rendered. Therefore, it is important to provide support devices on the baseplate 24 that will serve to counteract this tendency.

First of all, the patient is placed on the elongate pad or surface 12 in such maner as to require a stretching of the cervical spine slightly in order to properly position the patient's mastoid bone upon the mastoid support section. Typically, the height of the headrest member, as well as the tilt, has at this time already been approximately established, although additional minor changes are not necessarily ruled out. Then the doctors proceeds to increase the downward tilt of the headrest portion to a level that can be comfortably tolerated by the patient. The doctor thereafter swings the yoke to a location substantialy over the patient's head, into a position such that the pads 32 associated with the tripod 30 come in firm contact with the head.

At this point, the knobs 28 on each side of the yoke are tightened, so as to lock the yoke in this position. This being done, the knob 40 on the top of the yoke is tightened until the doctor becomes aware of a certain amount of pressure being applied, pressure sufficient to immobilize the cranium against undesired motion during treatment. If the doctor has had insufficient experience as will enable him to readily determine when a proper amount of pressure has been applied as a consequence of rotating the knob 40, he can often rely on the patient's comments as to the degree of tightness he or she is experiencing, or the doctor can grasp the patient's cranium with his hands and attempt, by the reasonable application of force, to bring about motion thereof.

At this time, the doctor will want to further restrain the head against possible motion by moving the facial-occipital restraining members 52a and 54a, respectively, in this instance, into such positions as previously described which can be comfortably tolerated by the patient. When these several indications reveal that the head has been properly immobilized, the doctor may desire to move the headrest restraining device laterally, or toward the patient's posterior, while the patient's head remains completely restrained by appropriately rotating knob 64 until such time as he feels or senses the patient's neck to be at an optimum and relaxed position; which movement typically has the tendency to temporarily relax certain cervical spine distortions, such as kyphosis or other conditions in which the normal anterior lordotic cervical curve is no longer present.

Following all these aforementioned steps, the doctor can proceed to apply adjustic thrust(s) to the atlas with the assurance that the efforts he or she expends will be satisfactorily received insofar as the subluxated condition of the upper cervical spine is concerned. Our experience has been that this type of treatment has been successful in over 90 percent of the cases of subluxations of the cervical spine encountered, although it is true that in many instances a limited number of such additional treatments have been necessary in order to substantially completely alleviate the patient's symptoms.

CONTROL PANEL

Turning to control panel 22, FIG. 20, it will be seen that it involves a POWER ON button 201, a set of control buttons 205 comprising HEIGHT UP button (S-1), HEIGHT DOWN button (S-2), TILT UP button (S-3), and TILT DOWN button (S-4), as well as SELECT-O-MATIC Button 105, and certain other components, discussed hereinafter. The height and tilt buttons are provided on their interior with electric bulbs, to permit the buttons to become illuminated on occasion.

As will be discussed at length, our novel machine is operative in three separate regimes, with the first regime involving the positioning of the headrest assembly 20 by the use of the HEIGHT UP and HEIGHT DOWN buttons, as well as the TILT UP and TILT DOWN buttons. As is obvious, by the appropriate manipulation of these buttons by the chiropractor, the headrest is caused to undertake positions of height and tilt that are appropriate for the patient that is to be treated. These buttons are connected to the circuitry of a control apparatus, described hereinafter, that is responsible for bringing about operation of the electrohydraulic power means as will bring about the desired height and tilt changes.

Also depicted in FIG. 20 are helical potentiometers 120 and 130, which are associated with height and tilt, respectively. These potentiometers may, for example, have clock faces and be manufactured by the Bourns Company of Riverside, Calif., under the name of Knobpot. They have outer knurled portions that can easily be rotated by the doctor to vary the setting of the potentiometers, as well as a change in the position of the hands shown on the face of the potentiometers. The potentiometers are in parallel with a source of regulated voltage and connected to a closed-loop control aparatus that also causes the height and tilt to be varied.

After a given patient has been treated, it is desired that the chiropractor be enabled to keep an accurate record of the headrest positions that were found appropriate for this patient. These positions can be ascertained in accordance with a second regime by utilization of the helical potentiometers 120 and 130, which serve as a reference voltage producing means. Without touching the height or tilt buttons, the chiropractor depresses the SELECT-O-MATIC Button 105 and holds it in the depressed position, while at the same time noting which one of the tilt button and which one of the height buttons become illuminated. Presuming the TILT UP button is illuminated, indicating that the potentiometer 130 is not at a null condition with respect to the potentiometer 142 associated with the tilt mechanism, but indicates that the physical tilt of the headrest in this instance is positioned tiltwise lower than that position which is displayed by the indicia on the Knobpot 130, and therefore, the chiropractor must rotate the exterior ring of the tilt potentiometer 130 in an appropriate manner in order to change the effective electrical value thereof so as to more nearly agree with that of the potentiometer 142. When, by rotation of the potentiometer 130, it has been brought to an electrical position identical to the electrical position of potentiometer 142, the other tilt button, the TILT DOWN button, will become illuminated at the same time, but with decreased brilliance.

Similarly, and in the same maner, while holding the SELECT-O-MATIC Button depressed, the chiropractor can bring the potentiometer 120 into a balanced condition with the potentiometer 141 by the appropriate manipulation of the potentiometer 120, until both of the height buttons have been caused to be illuminated at the same time. When this has been accomplished, the chiropractor can then take a reading directly off the faces of the potentiometers 120 and 130 and make a record of same. Presuming he has achieved the most appropriate headrest position for this patient during this initial visit, the chiropractor can be assured that the same height and tilt positions of the headrest assembly can be obtained quickly and accurately at the time of this patient's next visit, when this information is properly programmed back to the Knobpot potentiometers 120 and 130 as described hereinafter.

The third regime is associated with such return visit by this patient, when it is desired to again place the headrest assembly in the appropriate positions for such patient. With the power turned on, the chiropractor then rotates the potentiometers 120 and 130 until such time as the hands of the potentiometers are again in agreement with the readings taken at the conclusion of this patient's previous visit. Upon the completion of the potentiometer rotation, the chiropractor then momentarily depresses the SELECT-O-MATIC Button 105, which causes the machine to go into an automatic mode. In this mode, referred to as the third regime, the headrest assembly is caused to automatically undertake height and tilt positions that are consistent with the positions to which the potentiometers 120 and 130 have been rotated. It is to be noted that upon energizing the SELECT-O-MATIC Button 105, the lamp or lamps on each of the height and tilt circuits will become illuminated in such maner as to inform the doctor in which direction, respectively, the machine is to operate upon the releasing of button 105. Upon the headrest reaching these positions, the electrohydraulic power means is de-energized, with the solenoid valves 330, 331, 340, and 341 located in the hydraulic lines also being deactivated, thus to rigidly lock the headrest support assembly in the desired position.

OTHER TABLE DETAILS

Turning to FIG. 21, it will be noted that this is a view of the underside of our novel cervical side-posture table, in which the electric motor 310 and the hydraulic pump 320 are depicted. The motor is selectively reversible by means of circuitry described hereinafter, and the pump is bi-directional, having two principal ports. this means that when the motor drives the pump in one direction one of such ports is a pressure output port, whereas the other port is a suction port. Upon reversal of the electric motor, the one port become the suction port and the other port becomes the pressure supply port. These relationships will be made more apparent from FIG. 23 of the drawings, wherein the lines 321 and 322 are depicted.

Closely associated with the pump and motor is a pressure reservoir 325 adapted to contain a suitable quantity of hydraulic fluid, and the solenoid valves 330, 331, 340 and 341. These solenoid valves are normally closed and are opened electrically only at such times as the electrohydraulic power means is energized to bring about movements of the headrest by means of actuators 66 and 68.

Also visible in this figure is the housing 327, in which the bulk of the electronic circuitry is contained. Protruding from one side of the housing 327 are the knobs 216, 268, 214, 270, 212 and 272 associated with the presets discussed at length in connection with FIG. 26.

MANUAL AND AUTOMATIC CONTROL SYSTEM

Turnin now to FIG. 22, we have shown a greatly-simplified block diagram of the control system for our new cervical side-posture table, that will serve to explain in broad terms the three-regime operation thereof. As discussed hereinabove relative to the mechanical operation of our invention, a plurality of push buttons are provided to enable the chiropractor to selectively cause the headrest assembly to be raised or lowered, and moved in tilt in a manner appropriate to the treatment to be administered. As also set forth, the headrest is caused to move by double-acting hydraulic actuators, with actuator 66 being concerned with movements of the headrest in an up-and-down manner, and hydraulic actuator 68 being concerned with tilt movements of the headrest. These actuators as well as the hydraulic system 300 are depicted in FIG. 22 in conjunction with the other major components concerned with operation of our novel movable headrest.

The hydraulic system 300 is an electrohydraulic power system, which includes a controllable source of hydraulic pressure for the powering of the actuators, and is selectively controlled either by manual control 200 or automatic control 100. Circuits and devices integral with controls 200 and 100 are interlocked functionally as indicated by interlock control 210, with these serving to protect the power system from receiving contradictory control signals, as will be described in detail hereinafter.

As previously described with reference to FIG. 20, the control panel contains a set of manual control pushbutton switches indicated in FIG. 22 as buttons 205. It is to be noted that the chiropractor considers tilt of the baseplate 24 as being upward tilt or downward tilt with reference to the patient's head, and the tilt buttons are so marked. However, for purposes of more clearly explaining the mechanical and electrical operation of the automatic and manual control functions, the schematic diagrams discussed hereinafter will consider the TILT UP movement as a TILT RIGHT control, and the TILT DOWN movement as a TILT LEFT control. This alternative nomenclature will serve the important function of obviating confusion in the description of the respective TILT and HEIGHT movements.

The first regime of operation of our device is involved when manualy adjusting the headrest to accommodate a new patient for treatment. The manual control 200 in FIG. 22 utilizes a set of four momentary push-button switches 205, equipped with UP and DOWN buttons for height control and RIGHT and LEFT buttons for tilt control. It is allowable in accordance with our invention to have UP height movement and RIGHT tilt movement, or DOWN height movement and LEFT tilt movement, simultaneously. However, any other combination would cause damage to the power system and, advantageously, our interlock control function 210 positively prevents such improper operation. Similarly, operation of any manual control when the system is under automatic control instantly disables the automatic control 100, thereby preventing possible damage due to conflicting control commands to the power system.

Automatic control 100 includes the manually-adjustable, calibrated potentiometers 120 and 130 to be used in regime two to calibrate a selected headrest position and in regime three for automatic operation of this invention to adjust the headrest to a previously calibrated position; logic and control circuits for generating required control signals; momentary push-button start switch 105 (also known as a SELECT-O-MATIC switch); start switch pilot lamp 104; and a set of four indicator lamps 110 for push buttons 205. Automatic control 100 is associated with the second and third regimes of operation of our table.

In the second regime, the operator can advantageously determine the exact position of the headrest obtained from manual control by turning potentiometers 120 and 130 to a null position as defined hereinafter; inspecting the calibrated dials theeof at such null, and recording of the readings thus obtained. To perform this determination, start switch 105 is depressed and held closed. Electrical signals from position sensors 141 and 142 are indicative of the selected headrest position and are compared to the electrical signals from adjustable potentiometers 120 and 130 at the time switch 105 is closed. Note potentiometers 141 and 142 in FIGS. 7A and 7B. Assuming a difference in position for both potentiometers, either the UP or DOWN lamp, and either the RIGHT or LEFT lamp, of lamps 110 will be illuminated.

Continuing to hold switch 105 closed, the operator manually rotates potentiometer 120 in the direction indicated by the UP-DOWN lamps. At one setting of potentiometer 120, the electrical signals thus produced will exactly balance the signals from the position sensor 141 associated with the headrest height. This point is defined as the null position, and at this point the other UP-DOWN lamp will be illuminated and both lamps will be on, thereby indicating the balance or null condition to the operator. If, in spite of the balance indication, the operator continued to rotate potentiometer 120, the first UP-DOWN lamp would go out, indicating the need to reverse the direction of rotation to return the potentiometer 120 to the null or balance point.

Next, potentiometer 130 is manually adjusted in a similar manner to its balance point as indicated by simultaneous illumination of both RIGHT-LEFT lamps. The operator releases switch 105 and records the setting of potentiometer 120 and 130 from calibrated scales associated with each. In accordance with our invention, the recorded settings will permit automatic resetting of the headrest assembly to the manually adjusted position any time in the future, by turning potentiometers 120 and 130 to such settings and utilizing the third regime, now to be described.

Regime three is associated with automatically returning the headrest to a previously-calibrated position. To accomplish such resetting, the operator manually sets potentiometers 120 and 130 to the respective previously-recorded settings for the patient under treatment, depresses switch 105 momentarily, and releases it. This operation initiates the automatic control function wherein the electrical signals from adjustable potentiometers 120 and 130 are compared with electric signals from position sensors 141 and 142 associated with height and tilt, respectively. Assuming a difference is present, automatic control 100 generates control signals that energize and direct hydraulic systems 300 to drive actuators 66 and 68 in the directions required to balance position sensors 141 and 142 signals with potentiometers 120 and 130 signals. When both tilt and height signals balance, automatic control 100 is automatically de-energized, and actuators 66 and 68 are advantageously locked into the required position by closing of the solenoid valves illustrated in FIGS. 21 and 23.

Turning now to FIG. 23, manual control 200 and certain aspects of interlock control function 210 will be described. This section of our invention includes a latching-type pushbutton primary power switch 201 and DC supply 202. DC power supply 202 has a +24-volt output utilized to operate solenoids 332 and 342, as will be explained, a regulated +24-volt output for comparators 143 and 144, and potentiometers 120, 130, 141 and 142 depicted in FIG. 24; and +12 volts for automatic control 100 circuits. Electric motor 310 operates from the AC power line, and rotates in the forward direction when the FORWARD lead is energized and is reversed rotation when the REVERSE lead is energized.

Motor 310 drives hydraulic pump 320 having a closed hydraulic system with actuator 66 and 68 and associated valves and lines. When motor 310 is in its FORWARD rotation mode, pump 320 generates pressure on lines 321 and suction on line 322; whereas, reversing the direction of motor 310 causes pressure to be applied to line 322, and suction to be applied to line 321. Line 321 is connected to actuator 66 via line 323 and solenoid valve 331, and to actuator 68 via solenoid valve 341. In a like manner, the opposite port of actuator 68 is connected to line 322 via solenoid valve 340 and line 326, whereas the opposite port of actuator 66 is connected to line 322 via solenoid valve 330. As will be understood, pressure in line 321 reaching actuator 66 causes the rod 72 of this actuator to move in the UP direction, whereas pressure in line 321 reaching actuator 68 causes the rod 74 of this actuator to move to the RIGHT. Quite obviously, pressure from the pump cannot cause actuator 66 to move unless valves 331 and 330 are open, and actuator 68 cannot be caused to move unless valves 341 and 340 are open. Reversal of pump rotation will, quite understandably, reverse the movements of both actuators.

Multiple switch set 205 includes four independent momentary contact push-button switch sections S-1, S-2, S-3 and S-4, as will be seen in FIG. 23. Each section consists of a set of contacts A, B, and C controlling AC circuits, and a set of contacts D, E, and F controlling DC circuits. Lamp set 110 has a bulb associated with each section, preferably contained within the push button, where the push buttons are formed of a translucent plastic. Lamp set 110 is controlled from automatic control 100 as described hereinafter.

Turning first to control of AC power to the FORWARD and REVERSE windings of motor 310, it is to be understood that motor 310 is controllable by either manual switches 205 or automatic control 100, and that such control must be mutually exclusive to prevent possible damage. For automatic operation, we have provided relays 106 and 107 operated by current from automatic control 100 to control motor 310 in the FORWARD and REVERSE directions, respectively, by means of the associated normally-open relay contacts 101 and 102. Diodes 108 and 109 absorb inductive surges from relays 106 and 107 for protection of the electronic circuits. Contacts 101 and 102 receive AC power via a series connection of normally-closed contacts C on switch set 205. As may now be recognized, depressing any of the push-button switches S-1 through S-4 will open its C contacts, removing power from relay contacts 101 and 102. Manual control of the motor is obtained by selectively depressing one or two of the push-button switches as desired, closing normally-open contacts B of the selected switch or switches. If an automatic operation were in progress at such time, it would be terminated by the opening of contacts C and F of the depressed switch and would thus be overridden by the manual control, although this is not necessarily a normal operating mode.

It is to be further noted that a unique feature of our interlock manual control is that the UP button switch S-1 and RIGHT button S-3 can be operated simultaneously, since both require FORWARD operation of motor 310. However, if the UP button switch S-1 is depressed and the LEFT button switch S-4 is also depressed at the same time, conflicting FORWARD and REVERSE directions of motor 310 will be called for. Advantageously, we cause the AC power to be completely removed in such case by opening of the A contacts of switches S-1 and S-4 when both are attempted to be operated simultaneously.

Similarly, the DOWN and RIGHT buttons can be depressed simultaneously but operation of DOWN and RIGHT buttons at the same time interrupts the AC power.

The DC sections D, E, and F of switch 205 control solenoids 332 and 342, and also interlock with automatic control 100. For example, when UP button switch S-1 is depressed, normally-open contacts E are closed, providing a ground return to solenoid 332 which opens height control valves 331 and 330. In accordance with our invention, pump 320 rotates FORWARD, driving actuator 66 in the desired UP direction. Normally-closed contacts F on switch S-1 are simultaneously opened, breaking the series connection of all of the F contacts supplying +12-volt DC power to the automatic control 100, thereby completely disabling the automatic operation. As previously noted, UP control and RIGHT tilt control can be accomplished simultaneously; in such case, contacts E of switch S-3 energizes tilt solenoid 342, opening valves 340 and 341 to tilt actuator 68. It should be noted that connections are also provided from solenoids 332 and 342 to automatic control 200 (shown in FIG. 24) for control therefrom. Diodes 343 and 333 across solenoids 332 and 342, respectively, absorb the inductive surges from the solenoid coils, protecting switch contacts and circuitry in automatic control 100.

Turning now to FIG. 24, a simplified block diagram showing the basic elements of the automatic control circuit or closed loop control apparatus used in regimes two and three in accordance with our invention may be seen. The functions of these elements may best be understood by considering a regime three example. Position sensors 140 (FIG. 22) comprise potentiometer 141 associated with height actuator 66 and potentiometer 142 associated with tilt actuator 68, as previously mentioned. The positions of the wiper arms of potentiometers 141 and 142 and the voltages present thereon are directly proportional to the position of the respective actuators 66 and 68.

In accordance with regime three operation, the operator sets calibrated adjustable potentiometers 120 and 130 to the selected settings. At this point, start switch 105 is pushed and released, which causes the closing of power relay circuit 112 shown in FIG. 24. Relay 112 will lock up in the closed position as described more fully below, supplying power to all of the electronic control circuits. Operation of switch 105 accomplishes a second function of resetting logic circuits in the height and tilt control circuits.

The wiper arm of height potentiometer 120 connects to input 1 of voltage comparator 143, and the wiper arm of potentiometer 141 controlled by height actuator 66 contacts to input 2 of comparator 143. As may be understood, the voltage at input 2 is proportional to the height of the headrest. Comparator 143 is arranged to produce a logic ONE at its output when the voltage at input 1 is more positive than the voltage at input 2, and a logic ZERO when input 2 is more positive than input 1. For purposes of explanation, it will be assumed that input 1 is more positive than input 2, calling for an UP movement of actuator 66. Therefore, a ONE appears at the output of comparator 143.

The level at the output of comparator 143 (at the time switch 105 is activated) is stored in height memory circuit 118, and is also transferred to direction control 195 via lines 145 and 146, and conditioned for use therein as a height control signal. It is to be understood that the equivalent elements in the tilt circuits will generate a tilt control signal from memory circuit 117 simultaneously with the generation of the height control signal. However, the tilt control signal is indirectly applied to directional control circuit 195, as will be described hereinafter.

Returning to the height control signal, directional control circuit 195 will energize the FORWARD windings of motor 310 and height solenoid 332. Simultaneously, valves 330 and 331 will open, applying hydraulic pressure to the UP port of actuator 66, thereby raising the headrest. Actuator 66 also moves the wiper arm of potentiometer 141 toward its balance point with potentiometer 120. As the headrest reaches its preselected position, the wiper arm of potentiometer 141 will just reach the exact balance or null point with respect to the wiper arm of potentiometer 120. At this point, output of comparator 143 will change state from ONE to ZERO. Height transition detector circuit 116 compares this signal to the signal stored in memory 118 via line 147, thereby sensing this transition. Detector 116 thereupon inhibits direction control circuit 195, which releases height solenoid 332, closing valves 330 and 331, thereby locking actuator 66 at its preselected height. If no requirement exists at this time for actuation of tilt actuator 68, motor 310 will be turned off; otherwise, motor 310 will continue to operate appropriately until the correct tilt is achieved.

Turning now to the tilt controls shown in FIG. 24, assume that input 1 to comparator 144 is more negative than input 2, producing a ZERO at its output. This condition, in accordance with our invention, requires a LEFT motion of the tilt control and therefore a REVERSE direction for pump 320. The signal from comparator 144 to tilt memory 117 produces a REVERSE direction control signal. This signal is applied to tilt scheduler circuit 180, which serves to prevent application of the REVERSE direction control signal to motor 310 until the FORWARD rotation required by the height control is completed. As may be noted, the height control signal is also applied to tilt scheduler circuit 180 acting to inhibit the tilt REVERSE direction control signal from directional control 195. When height transition detector 116 detects the height balance condition as previously described, the change stops the FORWARD motor rotation and releases the tilt REVERSE direction control signal from tilt schedule 180 via delya 190 to directional control 195. Delay circuit 190 produces a short delay to allow motor 310 to come to a complete stop prior to reversing. In response to the tilt REVERSE direction control signal released from scheduler 180, directional control 195 simultaneously energizes tilt solenoid 342, opening valves 340 and 341, and operates motor 310 in the REVERSE direction. The hydraulic fluid under pressure from pump 320 thus enters the LEFT port of actuator 68, tilting the headrest to the left. In a like manner as previously described for the height control, actuator 68 moves the wiper arm of potentiometer 142 to a balance point with adjustable potentiometer 130, at which time motor 310 stops and tilt solenoid 342 is de-energized. Valves 340 and 341 close, locking actuator 68 in position.

Relay disconnect circuit 114 receives the cutoff signal from height transition detector 116 and then from tilt transition detector 115. At this point, the presence and coincidence of both signals causes disconnect circuits 114 to release power relay circuit 112, thereby removing all power from the control circuit electronics.

In the example just described, the height control required FORWARD rotation of the motor, and the tilt control required REVERSE rotation. Tilt scheduler 180, as described, correctly sequences these controls consecutively in this instance. However, when both height and tilt control signals require the same motor rotation, the height and tilt control signals applied to tilt scheduler 180 are coincident and allow the tilt control signal to be immediately applied to the delay 190, thence to direction control circuit 195, energizing tilt solenoid 342 after a short delay, thereby sequencing the controls to operate substantially simultaneously.

Having described the functions of each basic element of our automatic control circuits, the details of each element will now be explained by reference to FIG. 25.

After setting variable potentiometers 120 and 130 for the desired headrest position, the chiropractor depresses and releases start switch 105. As contacts of switch 105 are closed, power relay 125 is closed by current flow from the +12-volt power supply 202 (FIG. 23), through the relay coil 131 and disconnect diode 121 to ground through switch 105. Automatic pilot lamp 104 is illuminated from contacts 127 of relay 125, thus indicating the automatic operating mode. Contacts 127 also supply +12-volt power to all automatic control 100 electronic circuits, labeled "+V". The ground at the input of inverter 122 from switch 105 causes its output to go high, operating the reset inputs of flip-flop 166 of tilt transition detector 115, and flip-flop 156 of height transition detector 116. As inverter 122 output goes high, the output of inverter 123 will go low and capacitator 124 will rapidly discharge to ZERO through resistor 159. As switch 105 is released, disconnect diode 121 opens, allowing the input of inverter 122 to rise. The output of inverter 122 goes to ground, releasing the reset line to flip-flops 156 and 166. The input to inverter 123 is now low, and its output goes high. This level appears across resistor 159 of FIG. 25, since the voltage across capacitor 124 cannot change instantly. The voltage across resistor 159 is applied to the C (clock) inputs of flip-flops 152 and 162, causing these units to store at their Q outputs the level present at their D inputs. The clocking voltage decays exponentially through resistor 159, effectively grounding the C inputs, thereby storing the Q outputs for the remainder of the operation cycle. As is characteristic of the flip-flops 152 and 162, subsequent changes at the D inputs will have no further effect on the Q outputs.

The clocking action that occurs when switch 105 is released as previously described causes the Q-BAR outputs of flip-flops 156 and 166 to go to ZERO; these outputs are applied to NAND gate 157, causing its output to be high and turning on transistor switch 158, whose collector is returned to the positive source through relay contacts 126 and relay coil 131, thereby holding relay 125 closed after switch 105 is released. Diode 128 across relay coil 131 serves to absorb transients that could damage transistor switch 158 at turn-off.

As described previously, the outputs of comparators 143 and 144 of FIG. 25 are determined by the voltage relationships at their 1 and 2 inputs, and will be either ONE or ZERO. The level from coamparator 143 will be stored as the Q output from memory flip-flop 152, and the level rom comparator 144 will be stored as the Q output from memory flip-flop 162. These outputs will not change during the operating cycle. The established logic levels of Q and Q-BAR for flip-flops 152 and 162 disable NAND gates 153 and 154, and 163 and 164, respectively. These gates will be enabled when the driven potentiometers and the adjustable potentiometers are balanced, as will be described below.

Directional control circuits 195 control the FORWARD and REVERSE windings of motor 310 (FIG. 24). NAND gates 171 and 173 control the height direction, and NAND gates 172 and 174 control the tilt direction. Inverters 177 and 178, and gates 179 and 181 of FIG. 25, form a lockout function, preventing simultaneous activation of FORWARD and REVERSE windings. When gate 179 is energized, transistor switch 183 (which may be a 2N2222) closes FORWARD relay 106 (FIG. 23). Gate 181 is, in accordance with our invention, disabled when gate 179 is enabled and vice versa. Transistor switch 182 controls REVERSE relay 107 (FIG. 23). The control for height is determined by the output level of height comparator 143 appearing at gate 171, activating relay 106 for a ONE level and activating relay 107 for a ZERO level. The Q-BAR output from flip-flop 156 is inverted by inverter 129, which activates transistor switch 197, energizing height solenoid 332 (FIG. 23).

The control for tilt is determined by the output level of tilt comparator 144 appearing at gate 172 in FIG. 25. However, as previously discussed, tilt scheduler circuit 180 is used to inhibit the tilt control if height and tilt require opposite motor rotation. Exclusive OR gate 184 and NAND gates 185 and 186 are utilized for this purpose. If the Q outputs from both flip-flops 152 and 162 are equal, indicating the same direction of motor rotation is required, a ZERO output will appear at the output of gate 186 and, after a short delay, a ONE level will appear at the output of inverter 193. This level enables gate 172 or 174, depending on the required direction, and turns on transistor switch 196, energizing tilt solenoid 342 (FIG. 23). Therefore, both height and tilt movements can be accomplished at the same time, although the tilt action will start a short time after the height action, due to the delay always present from delay circuit 190 as explained below.

If the logic levels at comparators 143 and 144 are not the same, the height control will be energized as described above. However, the Q output from flip-flops 152 and 162 will be opposite, the output of exclusive OR gate 184 will be ONE, and gate 185 disables gate 186, thereby preventing the tilt solenoid 342 and the motor relay 107 of FIG. 23 from operating until the height adjustment is complete. When the height adustement is correct, the logic level at the output of comparator 143 will reverse, enabling gates 153 or 154 and 155, producing a pulse at the C input to transition detector flip-flop 156 of FIG. 25, thereby reversing the Q and Q-BAR output levels. This action disables the height gates 171 or 173, stopping motor 310 and releasing solenoid 332. The Q output disables gate 185, which enables gate 186, allowing the Q output from tilt flip-flop 166 to be applied to the delay circuit 190 and thereby affect the tilt control as previously described. The delay from delay cicuit 190 allows motor 310 to stop completely before directional control 195 calls for operation in the opposite rotation.

Delay circuit 190 consists of inverter 191, NAND gate 192, inverter 193, and capacitor 194. The logic signal through gate 192 is delayed for the time required for the voltage to change across capacitor 194, producing the desired short delay.

When the tilt control potentiometers 130 and 142 are balanced, the logic level reversal at the output of comparator 144 enables gates 163 or 164 and 165 of FIG. 25, thereby clocking flip-flop 166. The resulting reversal of Q and Q-BAR levels inhibits gates 172 or 174, stopping motor 310 and releasing solenoid 342. At this point, both inputs to NAND gate 157 are high and its output goes to ZERO, turning off transistor switch 158. This action releases power relay 125, removing all power from the electronic circuit and lamp 104, and the automatic headrest adjustment is complete.

The logic elements shown in FIG. 25 may be implemented with many available units, as will be evident to those skilled in the art. However, we prefer the following units, available from the National Semiconductor Corporation:

NAND Gates    MM74COO
Flip-flops    MM5613A
Exclusive OR    MM74C86
NOR Gates    MM74C02

All low-power transistors such as those used in switches 158, 183 and 182, are preferably type 2N2222 and high-power solenoid driver transistors used in switches 196 and 197 are type 2N3055.

Having described how the intricate functional operations of the electronic control system are accomplished for our cervical side-posture table being utilized in the third regime for automatically resetting the headrest to a previously determined position, the operation in the second, or calibrate, regime will now be explained. In addition, an alternative implementation of the control system involving three preset controls will be described that allows the chiropractor to quickly select and set the table to any one of three predetermined positions, in addition to a position determined by the adjustable controls.

FIG. 26 shows this part of our electronic control system. Selection of a preset position, or a position determined by the adjustable control, is accomplished by depressing any one of the momentary contact preset push-button switches 274, 276, or 278, or the momentary contact push-button switch 105, respectively.

Each of the preset potentiometers may have a screw-driver adjustment, as depicted in FIG. 26. To set the preset potentiometers to achieve selected headrest positions, the chiropractor manually adjusts the height and tilt of the headrest to a first position. He then depresses and holds switch 274 in its closed posion and adjusts preset potentiometers 216 and 268 to their null positions as indicated by lamps 110 as previously described with reference to potentiometers 120 and 130. The chiropractor can then follow the same procedure for selecting preset positions for the remaining two pairs of preset potentiometers preset 2 and preset 3 for both HEIGHT and TILT.

As an example, when preset position number 1, switch 274 is depressed and momentarily maintained, this action affects a 2-bit memory comprising flip-flops 295 and 297, which combine with decoding gates 293, 291, 279, and 277 forms the logic circuit equivalent of four interlocked mechanical latching relays. Specifically, gates 294 and 299 are enabled causing the Q output from flip-flop 297 to be ZERO and the Q output from flip-flop 295 to be ONE. This condition generates a ONE output from gate 293 and ZERO output from gates 291, 279, and 277.

It is to be understood that depressing switch 274 in addition to enabling the height and tilt comparator circuits as described above, also energizes power relay circuit 112 in same manner as previously described for SELECT-O-MATIC Switch 105 via its front contacts. Thus, the electronic control circuits are emergized to provide the automatic control for the preset positions.

Upon the release of switch 274 disables gates 294 and 299 leaving Q and Q-BAR outputs of flip-flops 295 and 297 unchanged. The ONE output from gate 293 is utilized for three functions. First, transistor switch 286 is energized, illuminating lamp 280 mounted within the number 1 preset button, P 1. Secondly, gate 240 is enabled, transferring the output of comparator 218 via gate 248 to height memory circuit 118. Comparator 218 is responsive to the relative positions of potentiometer 141 driven by height actuator 66 and preset number 1 potentiometer 216 and produces either a ONE or ZERO at its output. The signal from comparator 218 appearing at height control circuit 118 causing the hydraulic system 300 (FIG. 22) to change the height position of actuator 66 to the point at which the output voltage of potentiometer 141 is equal to the output voltage of preset potentiometer 216 in the same manner as previously described.

Third, a ONE appears at one input of gate 252, enabling that gate, transferring the output of comparator 260 to the tilt memory circuit 117. The output of comparator 260 is a ONE or ZERO as determined by the voltages from preset tilt potentiometer 268, and driven tilt potentiometer 142 driven by tilt actuator 68. The electronic control circuits operate as previously described to adjust the tilt of the headrest to the selected preset condition, nulling potentiometers 142 and 268. Thus, the electronic control circuits are energized to provide the automatic control for the preset position.

Having described the circuit action resulting from depressing switch 274 (P-1), the action from operation of the other switches shown in FIG. 26 may be seen from the following truth table:

| Switch | Gates Enabled | Q Outputs 297 | Q Outputs 297 | Output Gate Enabled |
|---|---|---|---|---|
| 105(S) | 296 – 299 | 0 | 0 | 277 |
| 274(P-1) | 294 – 299 | 0 | 1 | 293 |
| 276(P-2) | 296 – 298 | 1 | 0 | 291 |
| 278(P-3) | 294 – 298 | 1 | 1 | 279 |

As will now be clear, depressing switch 276 will cause the headrest to be automatically set to the positions called for by the selected adjustments of number 2 preset potentiometers 214 and 270; and depressing switch 278 will select the position determined by setting of number 3 preset potentiometers 212 and 272. Similarly, the lamp associated with the switch depressed will be illuminated. SELECT-O-MATIC Switch 105 operates in the same manner as the preset switches, causing comparators 143 and 144 to be gated to the automatic control circuits with lamp 104 being energized by transistor switch 292.

As may be recognized, the operations just described involve the third regime of our electronic control system. The second regime wherein initial calibration of the adjustable potentiometers is accomplished will now be described, with continued reference to FIG. 26. As discussed hereinabove, after the initial manual adjustment of the headrest for a patient, the potentiometer settings corresponding to such position must be determined. The operator depresses SELECT-O-MATIC Switch 105 holding it depressed. Assume for purposes of example that the output of height comparator 143 is then a ONE. This signal appears at inverter 151 producing a ZERO at inverter 271, which energizes transistor switch 263, thereby illuminating UP lamp L-1. The operator therefore rotates manually adjustable potentiometer 120 in the DOWN direction. As potentiometer 120 reaches the null point with respect to driven potentiometer 141, comparator 143 is operated in its linear or transition region with the result that its output voltage is approximately midway between the level representing a ONE and the level representing a ZERO. Inverters 151, 271, and 269 operate in a similar manner, partially energizing both transistor switches 261 and 263. Therefore, at this desired null point lamps L-1 and L-2 both are partially illuminated. As previously described, the calibrated dial reading of the potentiometer 120 can then be utilized to determine, if the doctor wishes, the 'simulated' numerical position of the selected headrest position. With the preset button depressed, the null having been established with relation to potentiometers 216 and 268, at this time and before the headrest is allowed to move, the operator must depress and maintain the SELECT-O-MATIC Button 105 and release preset button 274, in this chronological order. Following this, the operator rotatively adjusts potentiometers 120 and 130 to again establish a null with reference to the selected position of the headrest for preset 1, thereby enabling him to record the simulated position from the clockface potentiometers as heretobefore described.

As will be understood, both potentiometers 120 and 130 are adjusted by the operator until both pairs of lamps, L-1 with L-2 and L-3 with L-4, are illuminated and nulled, respectively. Switch 105 is then released, and the power relay circuit 112 will release, since both height and tilt circuits are balanced, removing power from all control lamps. It should be noted at this point that during the calibration operation, holding switch 105 depressed maintains a reset signal on the height transition detector flip-flops 156 and 166 (FIG. 25), thereby preventing directional control 195 from energizing the hydraulic controls. As will be obvious, at a subsequent time the chiropractor can select Preset 2 position automatically by depressing switch 276 (P-2( momentarily, or select preset 3 position by depressing switch 278 (P-3) momentarily. The provision for three predetermined headrest positions in accordance with our invention is very advantageous to the chiropractor, since he can select standardized positions for specific problems and obtain accurate automatic adjustment to a selected position by momentarily depressing a single button.

We claim:

1. In a headrest assembly for use in treating patients, means for contacting the head of a patient and painlessly immobilizing the head against motion during treatment of the patient, one of said means being a contoured mastoid support member providing at least a portion of the support for the head and configured to contact and bear against a lower portion of the mastoid bone, and pressure applying means disposed above the level of said mastoid support member for applying pressure on another portion of the head, to assert force in a direction serving to cause additional pressure on the head against said mastoid support member, thus to effectively minimize unwanted head motion.

2. The headrest assembly as defined in claim 1 in which said pressure applying means is a yoke member generally of inverted U-shape, having tightening means thereon which can be selectively manipulated so as to control the amount of pressure sustained by said mastoid support.

3. The headrest assembly as defined in claim 1 in which a contoured cephalic support member is used adjacent said mastoid support member, said cephalic support member being contoured so as to contact the parietal region of the head and having a supporting base, said cephalic support member being movable so as to change the spacing with respect to said mastoid support, so as to enable various head sizes to be accommodated.

4. The headrest assembly as defined in claim 3 in which securing means are provided for locking the base of said cephalic support member in the selected position.

5. A cervical side-posture table for treating patients, comprising a body portion designed to support the torso and legs, and a movable headrest assembly, adjacent said body portion, for supporting the patient's head, said headrest assembly having a baseplate upon which a plurality of head-supporting and restraint members are operatively mounted, one such member being a contoured mastoid support removably mounted on said baseplate, said mastoid support being configured to contact and support at least a portion of the weight of the head, and to bear against a lower portion of the patient's mastoid bone, and pressure applying means located at a level above said mastoid support means, for applying pressure in a direction so as to control the amount of pressure supported and reacted by said mastoid support.

6. The cervical side-posture table as defined in claim 5 in which said pressure applying means is a yoke member of inverted U-shape, supported by laterally opposite portions of said baseplate, said yoke member being movable to a variety of positions with respect to the patient's head, and having means thereon by means of which varying amounts of pressure may be applied to the head, and in turn to said mastoid support.

7. The cervical side-posture table as defined in claim 5, in which a contoured cephalic support is used adjacent said mastoid support, said cephalic support being movable upon said baseplate to any of a variety of positions with respect to said mastoid support, thus to enable various head sizes to be accommodated, and means for locking said cephalic support in the selected position.

8. The cervical side-posture table as defined in claim 5 in which facial and occipital supports are also mounted on said baseplate, said facial and occipital supports being movable into contact with facial and occipital portions of the head in order to prevent rolling of the head during treatment.

9. The cervical side-posture table as defined in claim 6 in which said baseplate is selectively movable in a lateral sense while the patient's head is restrained.

10. The cervical side-posture table as defined in claim 7 in which said baseplate is equipped with securing means for receiving said mastoid and cephalic supports, with a plurality of such supports of varying sizes and configurations being available to be selected from, and the chosen pair then inserted into said securing means.

11. In a cervical side-posture table, a headrest assembly movable in height and tilt, said headrest assembly comprising support members thereon for receiving the head of a patient to be treated, said support members including a contoured mastoid support capable of being removably secured in a fixed position on said headrest assembly, said mastoid support being configured to contact the lower portion of the cranium and bear against at least a portion of the lower part of the patient's mastoid bone, and a contoured cephalic support usable in concert with said mastoid support and movable with respect thereto to a variety of positions in which it can be fixed, thus to enable heads of various sizes to be accommodated, and means located at a level above the height of said mastoid and cephalic supports, for applying pressure in a direction to hold the head of the patient tightly against said supports.

12. The cervical side-posture table as defined in claim 11 in which said mastoid and cephalic support are each equipped with mounting bases, and securing means are provided for receiving said bases in selected positions.

13. The cervical side-posture table as defined in claim 11 in which a baseplate is a part of said headrest assembly, with said baseplate being laterally movable for selected amounts with respect to the remaining portion of said headrest assembly.

14. The cervical side-posture table as defined in claim 13 in which a plurality of mastoid and cephalic supports of varying sizes and configurations are available to be selected from, and said baseplate is equipped with securing means for receiving a selected pair of supports, and locking same in desired positions.

15. The cervical side-posture table as defined in claim 13 in which said pressure applying means is a yoke member of inverted U-shape, supported by laterally opposite portions of said baseplate, said yoke member being movable to a variety of positions with respect to the patient's head, and having means thereon by means of which varying amounts of pressure may be applied to the head, and in turn to said mastoid support.

16. The cervical side-posture table as defined in claim 13 in which facial and occipital supports are also mounted on said baseplate, said facial and occipital supports being movable into contact with facial and occipital portions of the head in order to prevent rolling of the head during treatment.

17. The cervical side-posture table as defined in claim 11 in which power operated means are connected to said headrest assembly, for selectively changing the positions thereof, and control means operatively connected to said power operated means, arranged to cause said headrest assembly to move in height and/or tilt to positions selected by an operator.

18. The cervical side-posture table as defined in claim 17 in which said control means includes secondary control means for automatically positioning said headrest assembly to a predetermined position.

19. A cervical side-posture table for holding the head of a person in a relatively fixed position during therapeutic treatment by an operator comprising:
 a. fixed means for supporting the torso and legs of the person, and a relatively movable headrest assembly,
 b. means on said headrest assembly for temporarily immobilizing the head of the person,
 c. power operated means operatively connected to said headrest assembly for changing the position thereof, and
 d. control means operatively connected to said power operated means, arranged to cause said headrest assembly to move to a position selected by the operator.

20. A cervical side-posture table as defined in claim 19 in which:
 a. said power operated means is arranged to change the height and/or the tilt of said headrest assembly with respect to said fixed means for supporting the torso and legs, and
 b. said control means includes one or more manually operable elements.

21. A cervical side-posture table as defined in claim 20 in which said control means also includes secondary control means for automatically positioning said headrest assembly to a predetermined position.

22. A cervical side-posture table as defined in claim 21 in which:
   a. said secondary control means includes manually settable elements having indicia associated therewith, and wherein the setting of said elements is indicative of such predetermined headrest assembly position, and
   b. calibrating means for determining the setting of said elements for any selected headrest position.

23. A cervical side-posture table as defined in claim 19 in which said power operated means includes:
   a. an electric motor capable of rotation in either direction,
   b. an hydraulic pump driven by said motor, said pump providing a source of hydraulic fluid under pressure, and
   c. hydraulic actuator means operatively connected to said pump and responsive to said pressurized fluid, said acutator means being coupled to said movable headrest assembly and arranged to selectively change the position thereof.

24. A cervical side-posture table as defined in claim 23 in which said actuator means is arranged to provide upward translation and/or upward tilt of said headrest in response to one direction of rotation of said motor and pump, and downward translation and/or downward tilt of said headrest in response to the opposite direction of rotation of said motor and pump.

25. A cervical side-posture table as defined in claim 23 in which said control means includes:
   a. first relay means for energizing said motor to run in one direction,
   b. second relay means for energizing said motor to run in the opposite direction,
   c. electrically operated control valves interposed between said pump and said hydraulic actuator means and arranged to function on occasion to limit the flow of said hydraulic fluid to and from said actuator means, and
   d. means for causing such one direction of rotation and such opposite direction of rotation to be mutually exclusive.

26. The cervical side-posture table as defined in claim 19 in which said means on said headrest assembly for immobilizing the head involves relatively movable mastoid and cephalic supports.

27. A cervical side posture table for therapeutic treatment of patients comprising:
   a. a body support surface having fixed and adjustable portions,
   b. rotary electro-hydraulic power means coupled to said adjustable portion and arranged to operate in a first direction of rotation, to make a first type of change in the height and angular position of said adjustable portion relative to said fixed portion, and in a second direction of rotation to make an opposite type of change in the height and angular position of said adjustable portion,
   c. means for making said first and second directions of rotation mutually exclusive, and
   d. electronic control means operatively connected to said electro-hydraulic power means, said control means including means for manually changing the height and/or tilt of said adjustable portion, as well as means for automatically returning said adjustable portion to a selected prior position.

28. a cervical side-posture table for therapeutic treatment of patients comprising:
   a. a body support surface having fixed and adjustable portions,
   b. electro-hydraulic power means coupled to said adjustable portion and arranged to change the height and angular position of latter portion relative to said fixed portion,
   c. said electro-hydraulic power means including reversible electric motor, an hydraulic pump driven by said motor, and hydraulic actuators coupled to said adjustable portions and operatively responsive to hydraulic fluid pressure generated by said pump,
   d. electronic control means means operatively connected to said electro-hydraulic power means, said control means including means for manually changing the height and/or tilt of said adjustable portion, as well as means for automatically returning said adjustable portion to a selected prior position,
   e. said electric control means including first relay means for causing said electric motor to operate in one direction of rotation, thus to make a first type of change in the position of said adjustable portion, and second relay means for causing said motor to operate in the opposite direction of rotation, thus to make an opposite type of change in the position of said adjustable portion, and solenoid-operated control valves interposed between said pump and said actuators and arranged to selectively inhibit on occasion, any movement of said actuators.

29. The cervical side-posture table as defined in claim 28 in which means are provided for making such one direction of rotation and such opposite direction of rotation mutually exclusive.

30. a cervical side-posture table as defined in claim 27 in which said electronic control means includes:
   a. a first pair of sensor means connected to said adjustable portion for producing a voltage proportional to the height of said portion and a voltage proportional to tilt of said portion,
   b. a second pair of sensor means having calibrated indices, said second pair of sensor means being manually operable and producing voltages proportional to the indexes to which said sensors are set, and
   c. comparison means connected to said first sensor means and said second sensor means, said comparison means producing control signals to said control means, for bringing about such motion of said adjustable portion as to reduce the voltage differences existing between respective first and second sensor means.

* * * * *